(12) United States Patent
Trivedi et al.

(10) Patent No.: US 10,562,920 B2
(45) Date of Patent: Feb. 18, 2020

(54) LN(III) AND GA(III) METALLACROWN COMPLEXES

(71) Applicants: The Regents of the University of Michigan, Ann Arbor, MI (US); Centre National de la Recherche Scientifique, Paris (FR)

(72) Inventors: Evan R. Trivedi, Ann Arbor, MI (US); Vincent L. Pecoraro, Ann Arbor, MI (US); Svetlana V. Eliseeva, Orléans (FR); Stépane Petoud, Orléans (FR); Chun Y. Chow, Ann Arbor, MI (US); Tu Ngoc Nguyen, Ann Arbor, MI (US); Jacob Charles Lutter, Ypsilanti, MI (US); Ivana Martinic, Orléans (FR)

(73) Assignees: THE REGENTS OF THE UNIVERSITY OF MICHIGAN, Ann Arbor, MI (US); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 25 days.

(21) Appl. No.: 15/566,058

(22) PCT Filed: Apr. 18, 2016

(86) PCT No.: PCT/EP2016/058587
§ 371 (c)(1),
(2) Date: Oct. 12, 2017

(87) PCT Pub. No.: WO2016/166380
PCT Pub. Date: Oct. 20, 2016

(65) Prior Publication Data
US 2018/0127438 A1    May 10, 2018

Related U.S. Application Data

(60) Provisional application No. 62/149,047, filed on Apr. 17, 2015.

(51) Int. Cl.
*C07F 5/00* (2006.01)
*C07F 19/00* (2006.01)

(52) U.S. Cl.
CPC .............. *C07F 5/00* (2013.01); *C07F 5/003* (2013.01); *C07F 19/00* (2013.01)

(58) Field of Classification Search
None
See application file for complete search history.

(56) References Cited

FOREIGN PATENT DOCUMENTS

WO    2015035196 A1    3/2015

OTHER PUBLICATIONS

Azar, M.R., et al., "Controllable Formation of Heterotrimetallic Coordination Compounds: Systematically Incorporating Lanthanide and Alkali Metal Ions into the Manganese 12-Metallacrown-4 Framework", Inorganic Chemistry, Jan. 2014, pp. 1729-1742 (Year: 2014).*
Jankolovits, J.M., et al., "Using the Structural Versatility of Lanthanide Metallacrowns to Tune Anion Recognition, Self-Assembly, and Luminescence Properties", U of M Thesis, 2012, pp. 1-259 (Year: 2012).*
Reddy, M.L., et al., "Lanthanide benzoates: a versatile building block for the construction of efficient light emitting materials", Dalton Transactions, 2013, pp. 2663-2678 (Year: 2013).*
Zaleski, C.M., et al., "Synthesis, Structure, and Magnetic Properties of a Large Lanthanide—Transition-Metal SingleMolecule Magnet", Angew. Chem. Int. Ed., 2004, pp. 3911-3914 (Year: 2004).*
Karlin, K.D., et al., "Progress in Inorganic Chemistry", John Wiley and Sons, 1997, pp. 166-167 (Year: 1997).*
Lah et al., "The Fused Metallacrown Anion Na2{[Na0.5[Ga(salicylhydroximate)]4]2(µ2-OH)4}—is an Inorganic Analogue of a Cryptate", Journal of the American Chemical Society, 1993, pp. 5857-5858, vol. 115, No. 13.
PCT Application No. PCT/EP2016/058587, International Search Report, dated Jul. 18, 2016, 5 pages.

* cited by examiner

*Primary Examiner* — Michael G. Hartley
*Assistant Examiner* — Lance W Rider
(74) *Attorney, Agent, or Firm* — Soquel Group LLC

(57) ABSTRACT

The present invention concerns heterometallic metallacrown compounds incorporating Ga(III) and Ln(III) cations, with a templating ligand such as salicylhydroxamic acid or derivatives thereof, wherein said metallacrown contains at least one repeating [—Ga—N—O—] sub-unit where the N—O derives from the templating ligand.

11 Claims, 31 Drawing Sheets

LN(III) AND GA(III) METALLACROWN COMPLEXES

The present invention concerns Ln(III) and Ga(III) metallacrown complexes, and uses thereof.

Optical devices, bioanalytical assays, and biological imaging probes often utilize components that exhibit optical properties, such as organic fluorophores and semi-conductor nanoparticles. Some desired optical properties include long luminescence lifetimes, large effective energy differences between excitation and emission bands, and sharp emission bands throughout the visible and near-infrared (NIR) spectral ranges. Lanthanide(III) metal ions (Ln(III) or $Ln^{3+}$) contain 4 f orbitals and exhibit unique luminescent characteristics that fulfill entirely the aforementioned requirements for optical materials. However, most f-f transitions of $Ln^{3+}$ ions are forbidden by quantum mechanics rules inducing low absorption coefficients, resulting in inefficient direct excitation and requiring sensitization with an appropriate antenna.

The antenna sensitization strategy has led to the development of a wide variety of $Ln^{3+}$ based luminescent complexes formed with organic ligands, inorganics complexes and semi-conductors materials. In these complexes, among other parameters, the energy difference ($\Delta E$) between the ligand's excited triplet state ($T_1$) and the accepting f-orbital electronic level of the lanthanide impacts the global sensitization ability of the antennae.

The aim of the present invention is to provide luminescent lanthanide complexes.

The aim of the invention is to provide lanthanide complexes with remarkable luminescence properties across the visible and near-infrared (NIR) regions.

The present invention relates to metallacrowns incorporating Ga(III) and Ln(III) cations.

For ideal $Ln^{3+}$ based luminescent complexes, it is believed that a good strategy should balance the sensitization efficiency of the $Ln^{3+}$ and the protection from the presence of sources of non-radiative deactivation (due to harmonic combinations of —OH, —NH and —CH vibrations of the solvent molecules and of the organic ligands of the complex). The closer the $Ln^{3+}$ is to the organic chromophoric ligand environment, the larger the efficiency of the sensitization to the $Ln^{3+}$. At the same time, the closer the $Ln^{3+}$ gets to the quenching vibrations of the chromophore, the stronger the non-radiative deactivation. It is believed that the use of rigid systems in the complexes may allow for control of the distance between the antennae and the luminescent lanthanide(III) cations.

The examples disclosed herein are heterometallic metallacrowns which incorporate $Ga^{3+}$ ions.

Metallacrowns are metal complexes made with tetradentate ligands that cyclize to form a repeating [-M-N—O—]$_x$ sub-unit, where M is a cationic metal that serves as the metallacrown ring metal. Similar to crown ethers, metallacrowns can be synthesized with a range of sizes, and the inward facing oximat oxygen atoms are capable of binding to a central metal ion.

$Ga^{3+}$ ions are an isoelectronic cation to $Zn^{2+}$ that cannot interfere (quench) with the excited states of luminescent lanthanide. It is believed that the $Ga^{3+}$ metallacrowns disclosed herein possess many electronic features similar to $Zn^{2+}$ metallacrowns, while allowing for the use of different chromophores (e.g., tri-anionic metallacrown ligands to compensate for the charge of $Ga^{3+}$).

The $Ga^{3+}$ ring metal forms the backbone of the heterometallic metallacrowns disclosed herein. Various isotopes of gallium have been used for diagnostics and therapeutic biomedical applications. As such, the heterometallic metallacrowns disclosed herein may serve as multipurpose chemical agents. Furthermore, the combination of luminescent $Ln^{3+}$ and radioisotopes of $Ga^{3+}$ allows for the prospect of the heterometallic metallacrowns and complexes being used as both bimodal imaging (the radioisotope $^{68}Ga^{3+}$ is used in PET imaging) and theranostic (other isotopes of $Ga^{3+}$ can be used as potential therapeutic radionuclide) agents.

The present invention relates to a heterometallic metallacrown compound incorporating Ga(III) and Ln(III) cations, said metallacrown containing at least one repeating [—Ga—N—O—] sub-unit.

The present invention relates to a heterometallic metallacrown compound incorporating Ga(III) and Ln(III) cations, with a templating ligand such as salicylhydroxamic acid or derivatives thereof. The said metallacrown contains at least one repeating [—Ga—N—O—] sub-unit where the N—O derives from the templating ligand.

According to one embodiment, the heterometallic metallacrown compound according to the invention includes a Ln(III)[12-MC$_{Ga}{}^{III}{}_{N(shi)}$-4] core, wherein MC$_{Ga}{}^{III}{}_{N(shi)}$ is a metallacrown macrocycle with a repeating sub-unit consisting of Ga(III) ion and a salicylic hydroxamic acid (H$_3$shi) ligand or its derivatives.

Within the present application, it is to be understood that $Ln^{3+}$ may include any lanthanide ion, such as yttrium ($Y^{3+}$), lanthanum ($La^{3+}$), cerium ($Ce^{3+}$), praseodymium ($Pr^{3+}$), neodymium ($Nd^{3+}$), promethium ($Pm^{3+}$), samarium ($Sm^{3+}$), europium ($Eu^{3+}$), gadolinium ($Gd^{3+}$), terbium ($Tb^{3+}$), dysprosium ($Dy^{3+}$), holmium ($Ho^{3+}$), erbium ($Er^{3+}$), thulium ($Tm^{3+}$), ytterbium ($Yb^{3+}$), or lutetium ($Lu^{3+}$).

According to an embodiment, the heterometallic metallacrown according to the invention may also include at least one counteraction ($C^+$) which balances the charge of the compound.

According to an embodiment, the heterometallic metallacrown according to the invention includes at least one ligand as bridging unit between the Ga(III) ion and the Ln(III) ion.

Preferably, said ligand contains at least one carboxylate group COO$^-$. Among such ligands, one may cite ligands of formula R—COO$^-$, wherein R may be chosen from ($C_6$-$C_{10}$)aryl groups or ($C_1$-$C_6$)alkyl groups, optionally substituted with an aryl group. In particular, R may be a substituted phenyl, substituted benzyl or substituted methyl group. Preferably, the ligand is a benzoate group.

As other carboxylate bridging units, one may cite isophthalate groups or derivatives thereof.

As derivatives thereof, one may cite groups having the following formula:

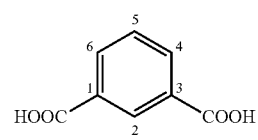

with any combination of R-groups bound at each of positions 2, and 4 through 6, each R-group being independently selected from the group consisting of —H, -D, —OH, —SH, —NH$_2$, —NO$_2$, —F, —Cl, —Br, —I, —CF$_3$, —OCH$_3$, —SO$_3$H, —CH$_3$, —CN, a fused aromatic ring, a fused heterocyclic ring, an amide, =O, =N, —N$_3$, —NR'H, —NR'2, —NR'$^{3+}$, —COOH, —COOR', —CH$_2$—R', —CHR$_2$, —CHR'R", —CR'R"R''', —OR', and combinations thereof, wherein R', R", and R''' are independently selected from any of the R-groups.

The present invention relates to a heterometallic metallacrown compound, having the formula: Ln(III)(OX)$_4$[12-MC$_{Ga}{}^{III}{}_{N(shi)}$-4](C$^+$), wherein MC$_{Ga}{}^{III}{}_{N(shi)}$ is a metallacrown macrocycle with a repeating sub-unit consisting of Ga(III) ion and a salicylic hydroxamic acid (H$_3$shi) ligand or its derivatives, OX$^-$ are bridging carboxylate units and C+ are countercations that balance the charge of the compound.

According to an embodiment, the above-defined [12-MC$_{Ga}{}^{III}{}_{N(shi)}$-4] unit includes four repeating [Ga(III)shi] sub-units that form a macrocyclic ring having twelve total atoms.

According to an embodiment, the heterometallic metallacrown compound according to the invention includes at least one ligand as bridging unit between the Ga(III) ion and the Ln(III) ion, wherein said ligand is H$_2$shi. According to this embodiment, the H$_2$shi acts as a bridge instead of the carboxylate units as mentioned above.

According to an embodiment, the heterometallic metallacrown compounds have the following formula: [Ga$_8$Ln$_2$(shi)$_8$(isophthalate)$_4$(DMF)$_6$]·8DMF·2H$_2$O. Such compounds may also be defined by the following formula: Ln$_2$(isophthalate)$_4$[12-MC$_{GaNshi}$-4]$_2$.

According to an embodiment, the heterometallic metallacrown compounds have the following formula: Ln$^{3+}$ [12-MC$_{Ga}{}^{III}{}_{N(shi)}$-4]. They also may be defined by the following formula: (LnGa$_4$(shi)$_4$(H$_2$shi)$_2$(C$_5$H$_5$N)$_4$(NO$_3$)).

According to an embodiment, the heterometallic metallacrown compounds have the following formula: Ga$_6$Ln(shi)$_9$ or [LnGa$_6$(shi)$_7$(Hshi)(H$_2$shi)(C$_6$H$_{16}$N)$_3$(C$_5$H$_5$N)$_2$]·xH$_2$O.

According to an embodiment, upon attachment of a targeting moiety or of a group, the heterometallic metallacrown exhibits a shift in its excitation wavelength.

Preferably, the heterometallic metallacrown is configured to emit visible luminescence, near-infrared luminescence, or combinations thereof.

In particular, upon attachment of a targeting moiety or of a group, the heterometallic metallacrown exhibits selective recognition of a cell, cellular substructure, tissue or tumor.

The present invention also relates to the use of the above-mentioned heterometallic metallacrown especially in bioanalytical assays or biological imaging, and also for multi-modal applications.

Within the present application, the templating ligand is salicylhydroxamic acid or derivatives thereof. As derivatives thereof, one may cite the following compounds:

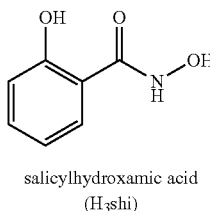

salicylhydroxamic acid (H$_3$shi)

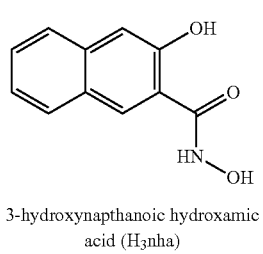

3-hydroxynapthanoic hydroxamic acid (H$_3$nha)

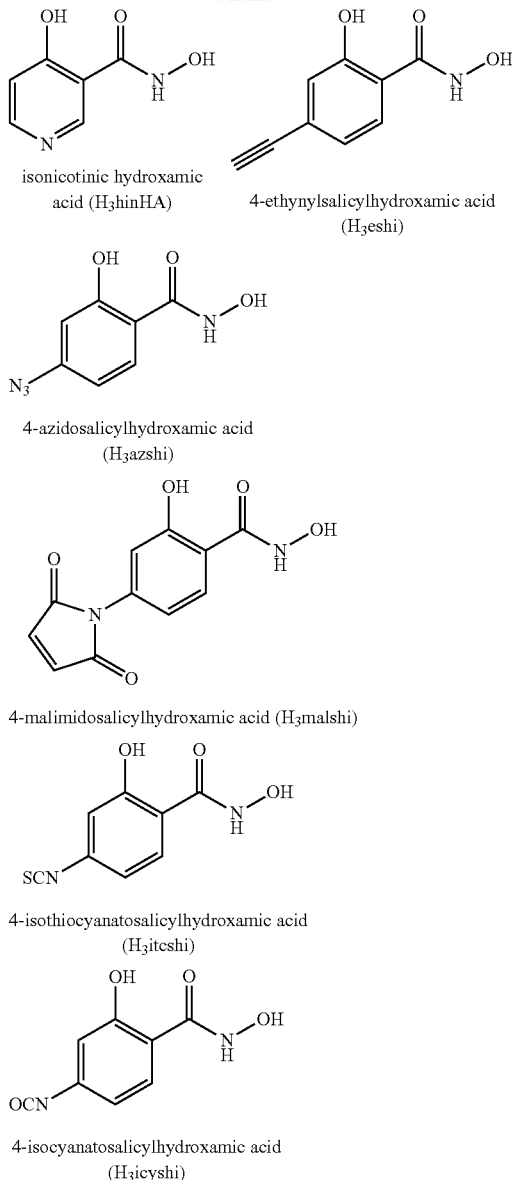

isonicotinic hydroxamic acid (H$_3$hinHA)

4-ethynylsalicylhydroxamic acid (H$_3$eshi)

4-azidosalicylhydroxamic acid (H$_3$azshi)

4-malimidosalicylhydroxamic acid (H$_3$malshi)

4-isothiocyanatosalicylhydroxamic acid (H$_3$itcshi)

4-isocyanatosalicylhydroxamic acid (H$_3$icyshi)

According to an embodiment, the hydroxamic acid ligand and derivatives thereof have the following formula:

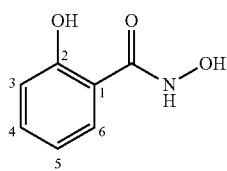

with any combination of R-groups bound at each of positions 3 through 6, each R-group being independently selected from the group consisting of —H, -D, —OH, —SH, —NH$_2$, —NO$_2$, —F, —Cl, —Br, —I, —CF$_3$, —OCH$_3$, —SO$_3$H, —CH$_3$, —CN, a fused aromatic ring, a fused heterocyclic ring, an amide, =O, =N, —N$_3$, —NR'H, —NR'2, —NR'$^{3+}$, —COOH, —COOR', —CH$_2$—R', —CHR$_2$, —CHR'R", —CR'R"R'", —OR', and combinations thereof, wherein R', R", and R'" are independently selected from any of the R-groups.

One example of the heterometallic metallacrown may be referred to herein as an Ga$_4$Ln(shi)$_4$ complex (Ln=Sm$^{3+}$, Eu$^{3+}$, Gd$^{3+}$, Tb$^{3+}$, Dy$^{3+}$, Ho$^{3+}$, Er$^{3+}$, Tm$^{3+}$, and Yb$^{3+}$), and has the formula [Ga$_4$Ln(shi$^{3-}$)$_4$(C$_6$H$_5$CO$_2$)$_4$(C$_5$H$_5$N)(CH$_3$OH)]·(C$_5$H$_6$N$^+$)·C$_5$H$_5$N·CH$_3$OH. The Ln$^{3+}$ is located at the core of the metallacrown and adopts a coordination number of eight. Its coordination is completed through a bond to the ring by benzoate ligands that create a bridge between Ln$^{3+}$ and Ga$^{3+}$ metal ions. In this complex, Ga$^{3+}$ is the ring metal and Ln$^{3+}$ is the central metal. The bridging benzoate ligands may play a role in the sensitization of the lanthanide(III) ions. The Ga$_4$Ln(shi)$_4$ complex may also be referred to as Ln$^{III}$(OBz)$_4$[12-MC$_{Ga^{III}N(shi)}$-4](pyr$^+$) using nomenclature analogous to crown ethers. The 12 specifies the 12-membered metallacrown ring that has 4 oxime oxygens that may bind to the central cation. MC is used to distinguish a metallacrown from a crown ether (C). The Ga(III) which is the ring metal is specified as a subscript to the MC designator as is N which represents the Nitrogen atom of the oxime which is also an integral component of the metallacrown ring. The ligand that templates the metallacrown is specified as an abbreviation. In this example, shi refers to salicylhydroxamic acid. The central metal is specified outside of the brackets defining the metallacrown to emphasize that the LnIII is captured in the center of the ring. Similarly, bridging anions (in this example benzoate (OBz)) that stabilize the binding of the central metal and also bond to the ring metal are indicated outside the brackets. Counter cations or counteranions not bound to the ring or central metal are designated after the brackets describing the metallacrown. The ring, [12-MC$_{Ga^{III}N(shi)}$-4], contains twelve atoms, and is a metallacrown macrocycle constituted by four repeating units consisting of Ga$^{3+}$ and the organic ligand salicylic hydroxamic acid (H$_3$shi) or derivatives thereof. Each of the synthesized Ga$_4$Ln(shi)$_4$ heterometallic metallacrowns exhibits lanthanide-based luminescence bands that are specific to the nature of the coordinated lanthanide as a result of an antenna effect located in the metallacrown architecture.

The following scheme is an example of the four-component supramolecular self-assembly process for forming of Ga$_4$Ln(shi)$_4$:

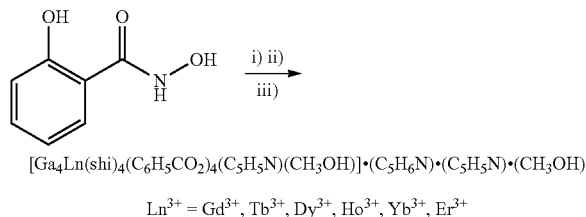

[Ga$_4$Ln(shi)$_4$(C$_6$H$_5$CO$_2$)$_4$(C$_5$H$_5$N)(CH$_3$OH)]·(C$_5$H$_6$N)·(C$_5$H$_5$N)·(CH$_3$OH)

Ln$^{3+}$ = Gd$^{3+}$, Tb$^{3+}$, Dy$^{3+}$, Ho$^{3+}$, Yb$^{3+}$, Er$^{3+}$

In this scheme, at i) salicylic hydroxamic acid, 1 eq. of Ga(NO$_3$)$_3$ xH$_2$O and 0.25 eq. Ln(NO$_3$)$_3$ xH$_2$O are dissolved in MeOH. Other example solvents include dimethylformamide (DMF), water, acetonitrile, and combinations thereof. At ii), 4 eq. of sodium benzoate are added and the solution is stirred. The solution is filtered, and at iii) pyridine is added. The solution is stirred again and filtered. Slow evaporation yields a crystalline compound.

FIGS. 1A and 1B illustrate the X-ray crystal structures of one example of the Ga$_4$Ln(shi)$_4$ heterometallic metallacrown where the lanthanide is dysprosium(III) Dy$^+$(BzO$_2$)$_4$[12-MC$_{Ga^{III}N(shi)}$-4] (pyr$^+$). A top-down along the pseudo C$_4$-axis is shown in FIG. 1A and a side view perpendicular to the c-axis is shown in FIG. 1B. Hydrogen atoms and lattice solvents have been removed for clarity. The other Ga$_4$Ln(shi)$_4$ complexes are identical in composition, except for the lanthanide cation.

Another example of the heterometallic metallacrown may be referred to herein as an Ga$_4$Ln(shi)$_6$ complex ([LnGa$_4$(shi)$_4$(H$_2$shi)$_2$(C$_5$H$_5$N)$_4$(NO$_3$)](C$_5$H$_5$N)$_2$ (Ln$^{III}$=Gd$^{III}$, Tb$^{III}$, Dy$^{III}$, and Ho$^{III}$) and [LnGa$_4$(shi)$_4$(H$_2$shi)$_2$(C$_5$H$_5$N)$_5$](NO$_3$)(C$_5$H$_5$N) (Ln$^{III}$=Er$^{III}$, Tm$^{III}$, and Yb$^{III}$)). The Ga$_4$Ln(shi)$_6$ complex contains a non-planar Ln$^{3+}$[12-MC$_{Ga^{III}N(shi)}$-4] core. The central Ln ion is bridged to two Ga$^{3+}$ ions by two H$_2$shi$^-$ ligands. In the case of Gd$^{III}$, Tb$^{III}$, Dy$^{III}$, and Ho$^{III}$, the lanthanide coordination sphere is further filled by a chelating nitrate.

FIGS. 2A and 2B illustrate the X-ray crystal structure of one example of the [LnGa$_4$(shi)$_4$(H$_2$shi)$_2$(C$_5$H$_5$N)$_4$(NO$_3$)](C$_5$H$_5$N)$_2$ heterometallic metallacrowns (i.e., [TbGa$_4$(shi)$_4$(H$_2$shi)$_2$(C$_5$H$_5$N)$_4$(NO$_3$)] (C$_5$H$_5$N)$_2$) and its Tb$^{3+}$[12-MC$_{Ga^{III}N(shi)}$-4] core. Hydrogen atoms and lattice solvents have been removed for clarity. FIGS. 2C and 2D illustrate the X-ray crystal structure of one example of the [LnGa$_4$(shi)$_4$(H$_2$shi)$_2$(C$_5$H$_5$N)$_5$](NO$_3$)(C$_5$H$_5$N) heterometallic metallacrowns (i.e. [YbGa$_4$(shi)$_4$(H$_2$shi)$_2$(C$_5$H$_5$N)$_5$](NO$_3$)(C$_5$H$_5$N)) and its Yb$^{3+}$[12-MC$_{Ga^{III}N(shi)}$-4] core.

Through further modification of reaction conditions (i.e., solvent, stoichiometry, etc.) a third heterometallic metallacrown complex, Ga$_6$Ln(shi)$_9$ (Ln=Pr$^{3+}$, Nd$^{3+}$, Sm$^{3+}$, Gd$^{3+}$, Tb$^{3+}$, Dy$^{3+}$, Ho$^{3+}$, Er$^{3+}$, and Yb$^{3+}$), can be synthesized. The X-ray crystal structure of the Tb$^{3+}$ analog (FIG. 19A) shows a brand new [M-N—O] motif core structure (FIG. 19B). Hydrogen atoms and lattice solvents have been removed for clarity. While metallacrowns are considered to be structural analogs to crown ethers, this complex is analogous to cryptands.

For example, the core [M-N—O] motif of the complex may be compared to 1,10-diaza-2,5,8,12,15,18,20-heptaoxabicylco[8.8.2]icosane (FIG. 19C). Following the cryptate nomenclature, this complex may be described as a Ga(III) [3.3.1] metallacryptand, where Ga2 and Ga5 are considered to be analogous to the nitrogen atoms in a cryptand (FIG. 19C). In combination with metallacrown nomenclature we arrive at the shorthand [Tb(Hshi)(H$_2$shi){[3.3.1.]MC-20-$_{Ga^{III}N(shi)}$-7}(C$_5$H$_5$N)](C$_6$H$_{16}$N)$_3$. The central metal is the terbium ion, the six gallium ions and seven of the shi$^{3-}$ make up the metallacryptate, where there are twenty atoms in the [Ga—N—O] motif, seven of which are oxygens that are distributed across three cryptand-like "arms" in a 3:3:1 ratio. The remaining two shi ligands bridge gallium ions to the terbium, one is singly deprotonated and bridges Ga4 to Tb1 in a "standing up" conformation, the other is doubly deprotonated and bridges Ga3 and Ga6 to the Tb in a "laying down" conformation (FIG. 19A). There is a coordinated pyridine on Ga1. Three triethylammonium cations provide charge balance.

Other heterometallic metallacrowns may be formed with isophthalate bridging compounds.

For example, [Ln$_2$Ga$_8$(shi)$_8$(isophthalate)$_4$(C$_3$H$_7$NO)$_6$](C$_3$H$_7$NO)$_8$(NH$_4^+$)$_2$ complexes (Ln=Pr$^{3+}$, Nd$^{3+}$, Sm$^{3+}$, Eu$^{3+}$, Gd$^{3+}$, Tb$^{3+}$, Dy$^{3+}$, Ho$^{3+}$, Er$^{3+}$, Tm$^{3+}$, and Yb$^{3+}$) may be formed. FIG. 4 illustrates the X-ray crystal structure of one example of the [Ln$_2$Ga$_8$(shi)$_8$(isophthalate)$_4$(C$_3$H$_7$NO)$_6$](C$_3$H$_7$NO)$_8$(NH$_4^+$)$_2$ heterometallic metallacrowns (i.e. [Dy$_2$Ga$_8$(shi)$_8$(isophthalate)$_4$(C$_3$H$_7$NO)$_6$](C$_3$H$_7$NO)$_8$(NH$_4^+$)$_2$). These Ln$_2$Ga$_8$ complexes can also be formed using derivatives of isophthalate such as 5-maleimido-isophthalate (mip$^{2-}$) and 5-isothiocyanateisophthalate (itip$^{2-}$) (FIG. 26). These functional groups are reactive to couple with amine and thiol-bearing molecules. When employing 5-sulfoisophthalate (sip$^{3-}$), [Na$_2$Ln$_2$Ga$_8$(shi)$_8$ (sip)$_4$(H$_2$O)$_{10}$] (C$_3$H$_7$NO)$_{14}$(C$_5$H$_6$N)$_2$ complexes (Ln=Nd$^{3+}$, Sm$^{3+}$, Eu$^{3+}$, Gd$^{3+}$, Tb$^{3+}$, Dy$^{3+}$, Ho$^{3+}$, Er$^{3+}$, Tm$^{3+}$, and Yb$^{3+}$) may be formed. FIG. 25 illustrates the X-ray crystal structure of [Na$_2$Dy$_2$Ga$_8$(shi)$_8$(sip)$_4$(H$_2$O)$_{10}$] (C$_3$H$_7$NO)$_{14}$ (C$_5$H$_6$N)$_2$.

As an extension of the examples shown, further modifications to the salicylhydroxamic acid and isophthalic acid ligands may be performed with the intention of tuning the ligand $T_1$ energy, or allowing for further coupling reactions. As explained above, such modifications include the extension of the aromatic ring of shi to naphthanoic hydroxamic acid, or the replacement of a CH unit with a nitrogen into the aromatic ring as shown in isonicotinic hydroxamic acid. Other modifications on shi and isophthalic acid include the addition of ethynyl, azido, isothiocyano, isocyano, and malimido substituents onto the aromatic rings.

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

FIG. 14A represents brightfield (left), NIR emission (center; $\lambda_{ex}$: 377 nm bandpass 50 nm filter, $\lambda_{em}$: long pass 805 nm filter, exposure time: 25 s) and merged (right) images.

Figure 1A:
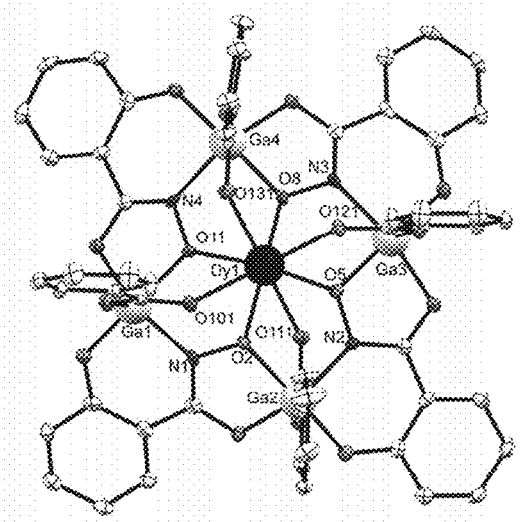
FIGS. 1A and 1B are the X-ray crystal structures of Ga$_4$Dy(shi)$_4$.

To further illustrate the present disclosure, examples are given herein. It is to be understood that these examples are provided for illustrative purposes and are to be construed as non-limiting.

EXAMPLES

Example 1

All reagents and chemicals were purchased from commercial sources and used without further purification. CHN analysis was performed by Atlantic Microlabs Inc. All reactions were carried under aerobic conditions.

Preparation of $Ga_4Ln(shi)_4$ Complexes $H_3shi$ (153.1 mg, 1.0 mmol), $Ln(NO_3)_3 \cdot xH_2O$ (0.25 mmol; 0.50 mmol for Ln=Sm and Eu), and $Ga(NO_3)_3 \cdot xH_2O$ (225.7 mg, 1.0 mmol) were dissolved in 40 mL methanol. Sodium benzoate (576.4 mg, 4.0 mmol) was added to the solution and stirred overnight. The solution was filtered, followed by addition of 2 mL pyridine. The solution was stirred for 15 minutes and then filtered. Slow evaporation of the half of the solution yielded crystalline compound after 2 weeks.

$[Ga_4Sm(shi)_4(C_6H_5CO_2)_4(C_5H_5N)(CH_3OH)] \cdot C_5H_6N \cdot C_5H_5N \cdot CH_3OH$ ($Ga_4Sm(shi)_4$). Yield: 104.9 mg (20.1%). ESI-MS, calc. for $[M]^-$, $C_{56}H_{36}N_4O_{20}GdGa_4$, 1519.8; found, 1519.8. Anal. Calcd for $SmGa_4C_{73}H_{60}N_7O_{22}$: C, 48.27; H, 3.33; N, 5.40. Found: C, 48.29; H, 3.16; N, 5.51.

$[Ga_4Eu(shi)_4(C_6H_5CO_2)_4(C_5H_5N)(CH_3OH)] \cdot C_5H_6N \cdot C_5H_5N \cdot CH_3OH$ ($Ga_4Eu(shi)_4$). Yield: 213.0 mg (20.1%). ESI-MS, calc. for $[M]^-$, $C_{56}H_{36}N_4O_{20}GdGa_4$, 1519.8; found, 1519.8. Anal. Calcd for $EuGa_4C_{73}H_{60}N_7O_{22}$: C, 48.22; H, 3.33; N, 5.39. Found: C, 48.35; H, 3.13; N, 5.58.

$[Ga_4Gd(shi)_4(C_6H_5CO_2)_4(C_5H_5N)(CH_3OH)] \cdot C_5H_6N \cdot C_5H_5N \cdot CH_3OH$ ($Ga_4Gd(shi)_4$). Yield: 91.8 mg (20.1%). ESI-MS, calc. for $[M]^-$, $C_{56}H_{36}N_4O_{20}GdGa_4$, 1519.8; found, 1519.8. Anal. Calcd for $GdGa_4C_{73}H_{60}N_7O_{22}$: C, 48.09; H, 3.32; N, 5.38. Found: C, 48.18; H, 3.07; N, 5.57.

$[Ga_4Tb(shi)_4(C_6H_5CO_2)_4(C_5H_5N)(CH_3OH)] \cdot C_5H_6N \cdot C_5H_5N \cdot CH_3OH$ ($Ga_4Tb(shi)_4$). Yield: 102.0 mg (22.4%). ESI-MS, calc. for $[M]^-$, $C_{56}H_{36}N_4O_{20}TbGa_4$, 1522.8; found, 1522.8. Anal. Calcd for $TbGa_4C_{73}H_{60}N_7O_{22}$: C, 48.04; H, 3.31; N, 5.37. Found: C, 48.33; H, 3.12; N, 5.54.

$[Ga_4Dy(shi)_4(C_6H_5CO_2)_4(C_5H_5N)(CH_3OH)] \cdot C_5H_6N \cdot C_5H_5N \cdot CH_3OH$ ($Ga_4Dy(shi)_4$). Yield: 106.6 mg (23.3%). ESI-MS, calc. for $[M]^-$, $C_{56}H_{36}N_4O_{20}DyGa_4$, 1525.8; found, 1525.8. Anal. Calcd for $DyGa_4C_{73}H_{60}N_7O_{22}$: C, 47.95; H, 3.31; N, 5.36. Found: C, 48.08; H, 3.10; N, 5.54.

$[HoGa_4(shi)_4(C_6H_5CO_2)_4(C_5H_5N)(CH_3OH)] \cdot C_5H_6N \cdot C_5H_5N \cdot CH_3OH$ ($Ga_4Ho(shi)_4$). Yield: 160.4 mg (35.0%). ESI-MS, calc. for $[M]^-$, $C_{56}H_{36}N_4O_{20}HoGa_4$, 1528.8; found, 1529.3. Anal. Calcd for $HoGa_4C_{73}H_{60}N_7O_{22}$: C, 47.88; H, 3.30; N, 5.35. Found: C, 48.01; H, 3.07; N, 5.50.

$[ErGa_4(shi)_4(C_6H_5CO_2)_4(C_5H_5N)(CH_3OH)] \cdot C_5H_6N \cdot 0.5C_5H_5N$ ($Ga_4Er(shi)_4$). Yield: 159.5 mg (36.2%). ESI-MS, calc. for $[M]^-$, $C_{56}H_{36}N_4O_{20}ErGa_4$, 1529.8; found, 1530.1. Anal. Calcd for $ErGa_4C_{69.5}H_{53.5}N_{6.5}O_{21}$: C, 47.38; H, 3.06; N, 5.17. Found: C, 47.29; H, 3.05; N, 5.53.

$[TmGa_4(shi)_4(C_6H_5CO_2)_4(C_5H_5N)(CH_3OH)] \cdot C_5H_6N \cdot 0.5C_5H_5N$ ($Ga_4Tm(shi)_4$). Yield: 148.4 mg (33.6%). ESI-MS, calc. for $[M]^-$, $C_{56}H_{36}N_4O_{20}TmGa_4$, 1532.8; found, 1532.8. Anal. Calcd for $TmGa_4C_{69.5}H_{53.5}N_{6.5}O_{21}$: C, 47.33; H, 3.06; N, 5.16. Found: C, 47.06; H, 2.95; N, 5.48.

$[YbGa_4(shi)_4(C_6H_5CO_2)_4(C_5H_5N)(CH_3OH)] \cdot C_5H_6N \cdot C_5H_5N \cdot CH_3OH$ ($Ga_4Yb(shi)_4$). Yield: 54.1 mg (11.8%). ESI-MS, calc. for $[M]^-$, $C_{56}H_{36}N_4O_{20}YbGa_4$, 1535.8; found, 1535.8. Anal. Calcd for $YbGa_4C_{73}H_{60}N_7O_{22}$: C, 47.67; H, 3.29; N, 5.33. Found: C, 47.69; H, 3.10; N, 5.49.

Preparation of $[Ln_2Ga_8(shi)_8(isophthalate)_4(C_3H_7NO)_6](C_3H_7NO)_8(NH_4^+)_2$ Complexes $H_3shi$ (306.3 mg, 2.0 mmol), $Ln(NO_3)_3 \cdot xH_2O$ (0.50 mmol), $Ga(NO_3)_3 \cdot xH_2O$ (511.5 mg, 2.0 mmol), and isophthalic acid (166.1 mg, 1.0 mmol) were dissolved in 15 mL DMF. Ammonium bicarbonate (632.5 mg, 8.0 mmol) was added to the solution and stirred overnight. The solution was filtered. Slow evaporation of the half of the solution yielded crystalline compound after 3 months.

$[Ga_8Pr_2(shi)_8(isophthalate)_4(DMF)_6] \cdot 8DMF \cdot 2H_2O$ ($Ga_8Pr_2(shi)_8$). Yield: 33.9 mg (3.6%). Anal. Calcd for $Pr_2Ga_8C_{130}H_{158}N_{24}O_{56}$: C, 41.17; H, 4.20; N, 8.86. Found: C, 40.98; H: 4.46; N: 9.22. Unit Cell: a=14.193 Å, b=17.696 Å, c=19.169 Å; α=113.22°, β=103.24°, γ=97.65°; V=4170.37 Å³.

$[Ga_8Nd_2(shi)_8(isophthalate)_4(DMF)_6] \cdot 8DMF \cdot H_2O$ ($Ga_8Nd_2(shi)_8$). Yield: 98.0 mg (10.4%). Anal. Calcd for $Nd_2Ga_8C_{130}H_{156}N_{24}O_{55}$: C, 41.30; H, 4.16; N, 8.89. Found: C, 40.96; H: 4.39; N: 9.36. Unit Cell: a=14.218 Å, b=17.725 Å, c=19.251 Å; α=113.19°, β=103.33°, γ=97.63°; V=4201.57 Å³.

$[Ga_8Sm_2(shi)_8(isophthalate)_4(DMF)_6] \cdot 8DMF \cdot 2H_2O$ ($Ga_8Sm_2(shi)_8$). Yield: 195.6 mg (20.5%). Anal. Calcd for $Sm_2Ga_8C_{130}H_{158}N_{24}O_{56}$: C, 40.97; H, 4.18; N, 8.82. Found: C, 40.67; H: 4.51; N: 8.96. Unit Cell: a=14.152 Å, b=17.741 Å, c=19.188 Å; α=112.91°, β=102.71°, γ=98.27°; V=4185.38 Å³.

$[Ga_8Gd_2(shi)_8(isophthalate)_4(DMF)_6] \cdot 8DMF \cdot H_2O$ ($Ga_8Gd_2(shi)_8$). Yield: 321.0 mg (33.7%). Anal. Calcd for $Gd_2Ga_8C130H_{156}N_{24}O_{55}$: C, 41.01; H, 4.13; N, 8.83. Found: C, 40.98; H: 4.28; N: 8.99. Unit Cell: a=14.104 Å, b=17.581 Å, c=19.217 Å; α=113.09°, β=102.60°, γ=98.35°; V=4134.44 Å³.

$[Ga_8Tb_2(shi)_8(isophthalate)_4(DMF)_6] \cdot 8DMF \cdot H_2O$ ($Ga_8Tb_2(shi)_8$). Yield: 329.8 mg (34.6%). Anal. Calcd for $Tb_2Ga_8C_{130}H_{156}N_{24}O_{55}$: C, 40.98; H, 4.13; N, 8.82. Found: C, 40.62; H: 4.45; N: 8.81. Unit Cell: a=14.105 Å, b=17.595 Å, c=19.248 Å; α=113.24°, β=102.63°, γ=98.16°; V=4142.24 Å³.

$[Ga_8Dy_2(shi)_8(isophthalate)_4(DMF)_6] \cdot 8DMF \cdot 2H_2O$ ($Ga_8Dy_2(shi)_8$). Yield: 280.1 mg (34.6%). Anal. Calcd for $Dy_2Ga_8C_{130}H_{158}N_{24}O_{56}$: C, 40.71; H, 4.15; N, 8.76. Found: C, 40.75; H: 4.45; N: 8.87. Unit Cell: a=14.1080 Å, b=17.5806 Å, c=19.2197 Å; α=113.107°, β=102.699°, γ=98.218°; V=4135.39 Å³.

$[Ga_8Ho_2(shi)_8(isophthalate)_4(DMF)_6] \cdot 8DMF \cdot 2H_2O$ ($Ga_8Ho_2(shi)_8$). Yield: 322.0 mg (33.7%). Anal. Calcd for $Ho_2Ga_8C_{130}H_{158}N_{24}O_{56}$: C, 40.66; H, 4.15; N, 8.75. Found: C, 40.31; H: 4.38; N: 9.02. Unit Cell: a=14.114 Å, b=17.658 Å, c=19.239 Å; α=113.06°, β=102.65°, γ=98.26°; V=4161.85 Å³.

$[Ga_8Er_2(shi)_8(isophthalate)_4(DMF)_6] \cdot 8DMF \cdot 2H_2O$ ($Ga_8Er_2(shi)_8$). Yield: 276.2 mg (28.7%). Anal. Calcd for $Er_2Ga_8C_{130}H_{158}N_{24}O_{56}$: C, 40.61; H, 4.14; N, 8.74. Found: C, 40.36; H: 4.42; N: 8.98. Unit Cell: a=14.092 Å, b=17.504 Å, c=19.208 Å; α=113.16°, β=102.51°, γ=98.25°; V=4112.80 Å³.

$[Ga_8Tm_2(shi)_8(isophthalate)_4(DMF)_6] \cdot 8DMF \cdot 2H_2O$ ($Ga_8Tm_2(shi)_8$). Yield: 235.0 mg (24.4%). Anal. Calcd for $Tm_2Ga_8C_{130}H_{158}N_{24}O_{56}$: C, 40.57; H, 4.14; N, 8.73. Found: C, 40.18; H: 4.26; N: 8.98. Unit Cell: a=14.148 Å, b=17.718 Å, c=19.296 521; α=113.08°, β=102.58°, γ=98.30°; V=4198.67 Å³.

$[Ga_8Yb_2(shi)_8(isophthalate)_4(DMF)_6] \cdot 8DMF \cdot 3H_2O$ ($Ga_8Yb_2(shi)_8$). Yield: 200.5 mg (20.7%). Anal. Calcd for $Yb_2Ga_8C_{130}H_{160}N_{24}O_{57}$: C, 40.30; H, 4.16; N, 8.68. Found: C, 39.92; H: 4.27; N: 8.88. Unit Cell: a=14.110 Å, b=17.700 Å, c=19.242 Å; α=113.05°, β=102.48°, γ=98.35°; V=4173.97 Å³.

Physical Methods

X-Ray Crystallography

Crystal data for the compounds $Ga_4Dy(shi)_4$, $Ga_4Tb(shi)_6$ (discussed further in example 2), and $Ga_6Tb(shi)_9$ were collected at 85(2) K on an AFC10K Saturn 944+ CCD-based X-ray diffractometer equipped with a Micromax007HF Cu-target microfocus rotating anode ($\lambda$=1.54187 Å), operated at 1200 W power (40 kV, 30 mA). The data were processed with CrystalClear 2.0 and corrected for absorption. The structure was solved and refined with the SHELXTL (version 6.12) software package. All non-hydrogen atoms were refined anisotropically. Hydrogen atoms placed in their idealized positions. For $Ga_4Tb(shi)_6$, the structure contained large solvent accessible voids totaling 834.1 Å$^3$ and 247.5 electrons per unit cell. This region had diffuse electron density and could not be modelled with any chemically reasonable moieties. The SQUEEZE routine of the PLATON suite of programs was applied to remove the diffraction contribution from these solvents.

Powder X-Ray Diffraction (PXRD)

Powder X-ray diffraction data for air-dried samples of the $Ga_4Ln(shi)_4$ complexes were collected at room temperature using a Bruker D8 Advance Diffractometer with Cu—$K_\alpha$ radiation (1.5406 Å, 40 kV, 40 mA). Powder diffraction patterns were collected at room temperature from 3° to 50° (2θ) using a step size of 0.05° and a scan time of 0.5 second/step.

Solid State Diffuse Reflectance

Solid state UV-Vis spectra were collected using an Agilent-Cary 5000 spectrophotometer equipped with a Praying Mantis diffuse reflectance accessory. Spectra were collected in reflectance mode, with $BaSO_4$ was used as a baseline. Samples (10% by weight) were mulled in $BaSO_4$ (90% by weight). The spectra were converted into normalized absorbance by using the equation A=1−R.

Solution Absorption Spectra

UV-Vis spectra for the compounds dissolved in methanol were recorded on a Cary 100Bio UV-Vis spectrophotometer. All spectra were collected in absorbance mode.

Photophysical Measurements

Luminescence data were collected on samples placed into 2.4 mm i.d. quartz capillaries or quartz Suprasil cells. Emission and excitation spectra were measured on a Horiba-Jobin-YvonFluorolog 3 spectrofluorimeter equipped with either a visible photomultiplier tube (PMT) (220-800 nm, R928P; Hamamatsu), a NIR solid-state InGaAs detector cooled to 77 K (800-1600 nm, DSS-IGA020L; Jobin-Yvon), or NIR PMTs (950-1450 nm, H10330-45; 950-1650 nm, H10330-75; Hamamatsu). All spectra were corrected for instrumental functions. Luminescence lifetimes were determined under excitation at 355 nm provided by a Nd:YAG laser (YG 980; Quantel), while the signal was detected in the NIR by the aforementioned PMT (H10330-75). The output signal from the detectors was then fed to a 500 MHz bandpass digital oscilloscope (TDS 754C; Tektronix) and then transferred to a PC for treatment with Origin 8®. Luminescence lifetimes are averages of at least three independent measurements. Quantum yields were determined with a Fluorolog 3 spectrofluorimeter according to an absolute method using an integration sphere (GMP SA). Each sample was measured several times under slightly different experimental conditions. Estimated experimental error for quantum yields determination is 10%.

Synthesis and Characterization $Ga_4Ln(shi)_4$ Complexes

Figure 1B:
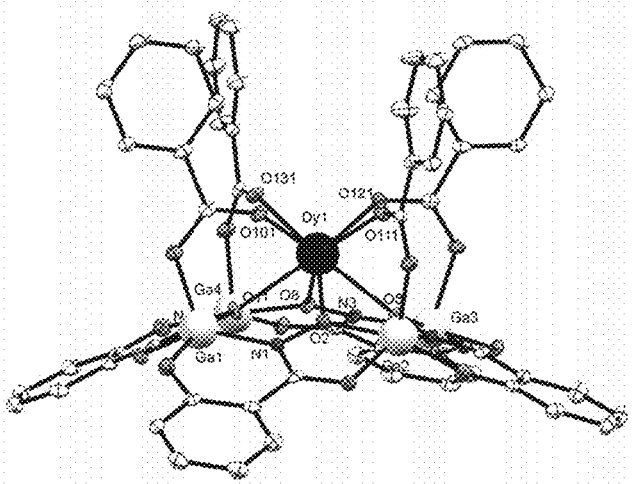

The reaction between shi, gallium(III) nitrate, lanthanide (III) nitrate, and sodium benzoate in a mixed methanol/pyridine solvent resulted in the formation of a metallacrown that adopts the 12-MC-4 topology, the negative charge of which is counter-balanced by a pyridinium cation. The success of this synthesis depends strongly on the size of the $Ln^{3+}$, with $Gd^{3+}$ being the largest ion that be can be incorporated. Larger ions may not fit within the cavity of the metallacrown resulting in lower thermodynamic stability. The X-ray crystal structure for the $Ga_4Dy(shi)_4$ compound is shown in FIGS. 1A and 1B. The X-ray crystal structure of $Ga_4Dy(shi)_4$ was determined to be in $P2_1/n$.

The other $Ga_4Ln(shi)_4$ complexes were determined to be identical in composition by elemental analysis, ESI-MS, and PXRD. For each metallacrown, four $shi^{3-}$ ligands coordinate four $Ga^{3+}$ ions to form the 12-MC-4 ring.

The central $Dy^{3+}$ ion is bridged to the ring by four benzoate ligands and adopts an 8-coordinate geometry which is close to a square antiprism. The pyridinium counter-cation was determined to be protonated to adjacent solvent molecules through hydrogen bonding.

In the previously reported $LnZn_{16}L_{16}$ structures, the distance between the $Ln^{3+}$ ion and the closest C—H oscillator was larger than 6 Å. The presence of high energy C—H, N—H, and O—H oscillators in close proximity to the $Ln^{3+}$ can lead to the quenching of the NIR luminescence. For $Ga_4Dy(shi)_4$, and the other analogues of the series, the shortest Ln-CH distance was found to be 4.37 Å. Nevertheless, remarkable NIR photophysical properties have been observed for these complexes despite this relatively short distance. This is a qualitative indication that the effect of potential luminescence quenching is compensated by the efficient chromophore to lanthanide energy transfer.

The centroid in the space between the four benzoate groups is ~2.3 Å from the nearest (i.e., closest) hydrogen atoms. Although no electron density was observed in that region, this void space is large enough to be occupied by a solvent molecule, which would potentially have implications in the photophysical data for the $Ga_4Ln(shi)_4$ complexes.

Figure 3:
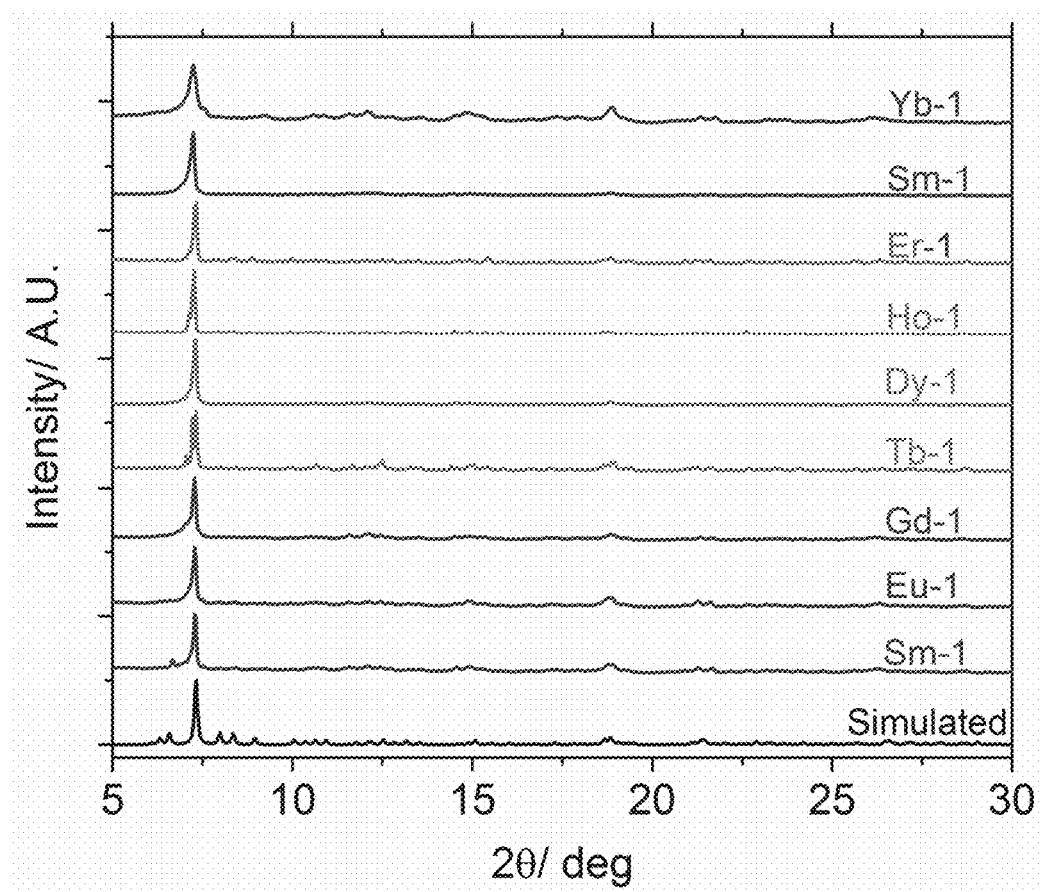
FIG. 3 is a graph illustrating the powder X-ray diffraction (PXRD) patterns of Ga$_4$Ln(shi)$_4$ complexes, with a simulated pattern obtained from the crystal structure of Ga$_4$Dy (shi)$_4$ shown in black.

The other $Ln^{3+}$ analogues were confirmed to be isostructural by powder X-ray diffraction (FIG. 3).

$Ga_8Ln_2(shi)_8$ Complexes

Figure 4:
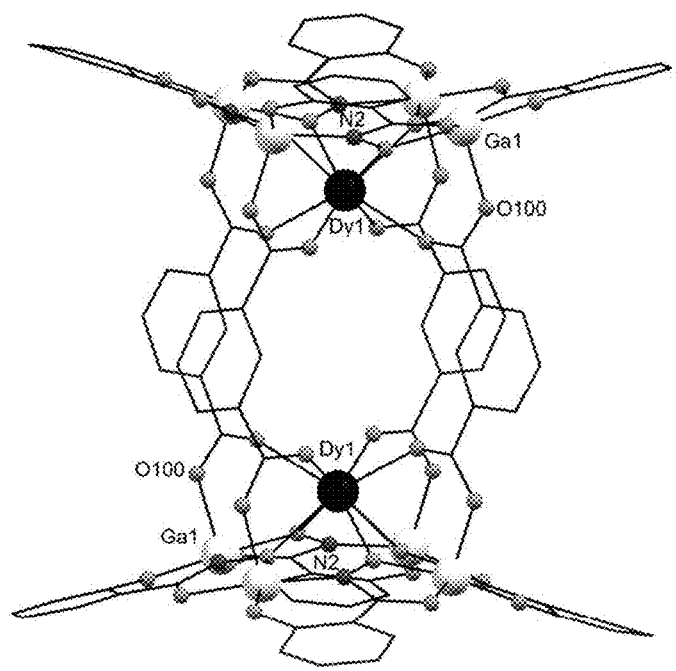
FIG. 4 is the crystal structure of Ga$_8$Dy$_2$(shi)$_8$ (Ln$^{III}$$_2$ (isophthalate)$_4$[12-MC$_{Ga}^{III}$$_{N(shi)}$-4]$_2$(NH$_4^+$)$_2$), where coordinating solvent molecules to the Ga(III) are omitted for clarity.

Utilizing a synthetic strategy, 12-MC-4 unit in the $Ga_4Ln(shi)_4$ complexes were linked together via isophthalate ligands. Using ammonium bicarbonate as a base, reaction of $H_3shi$, $Ln(NO_3)_3 \cdot xH_2O$, $Ga(NO_3)_3 \cdot xH_2O$ and isophthalic acid in DMF forms the $Ga_8Ln_2$ complex which can be described as two 12-MC-4 monomer subunits connected via four isophthalate groups (see FIG. 4). The molecular moiety has a net dianionic charge. Since no other metal atoms could be found in the electron density map, the charge is likely balanced by two lattice $NH_4^+$ ions. However, these counter-ions could not be located due to weak scattering. Similarly, the diffuse electron density of the lattice solvent required the use of SQUEEZE routine of the PLATON suite of programs.

TABLE 1

Crystallographic details for $Ga_8Dy_2(shi)_8$

|  | $Ga_8Dy_2$ |
|---|---|
| mol formula | $C_{96}H_{20}Dy_2Ga_8N_{12}O_{46}$ |
| Mw (g/mol) | 2939.84 |
|  | Triclinic/P-1 |
| T (K) | 85(2) |
| wavelength (Å) | 1.54178 |
| a (Å) | 14.1080(3) |
| b (Å) | 17.5806(3) |

TABLE 1-continued

Crystallographic details for Ga$_8$Dy$_2$(shi)$_8$

| | Ga$_8$Dy$_2$ |
|---|---|
| c (Å) | 19.2197(14) |
| α (deg) | 113.107(8) |
| β (deg) | 102.699(7) |
| γ (deg) | 98.218(7) |
| V (Å$^3$) | 4135.4(3) |
| Z | 1 |
| density, ρ (g/cm$^3$) | 1.180 |
| abs coeff, μ (mm$^{-1}$) | 6.713 |
| F(000) | 1408 |
| θ range for data collection (deg) | 2.62 to 68.24 |
| limiting indices | −16 ≤ h ≤ 16 |
| | −20 ≤ k ≤ 21 |
| | −23 ≤ l ≤ 23 |
| reflns collected/unique | 111713/14938 |
| completeness to θ (%) | 98.6 |
| no. of data/restraints/parameters | 14938/0/815 |
| goodness of fit on F$^2$ | 1.929 |
| final R indices | $R_1{}^a$ = 0.1430 |
| [I > 2σ(I)] | $wR_2{}^b$ = 0.3897 |
| R indices (all data) | $R_1{}^a$ = 0.1459 |
| | $wR_2{}^b$ = 0.3981 |
| largest diff peak and hole (e$^-$ Å$^{-3}$) | 12.150 and −2.064 |

$^a R_1 = \Sigma(||F_o| - |F_c||)/\Sigma|F_o|$.
$^b wR_2 = [\Sigma[w(F_o{}^2 - F_c{}^2)^2]/\Sigma[w(F°)^2]]^{1/2}$;
$w = 1/[\sigma^2(F_o{}^2) + (mp)^2 + np]$;
$p = [max(F_o{}^2, 0) + 2F_c{}^2]/3$ (m and n are constants);
$\sigma = [\Sigma[w(F_o{}^2 - F_c{}^2)^2]/(n - p)]^{1/2}$

TABLE 2

Selected bond lengths in the crystal structure of Ga$_8$Dy$_2$

| Bond | Length (Å) |
|---|---|
| Dy(1)—O(5) | 2.301(10) |
| Dy(1)—O(2) | 2.326(8) |
| Dy(1)—O(112) | 2.328(9) |
| Dy(1)—O(111) | 2.343(8) |
| Dy(1)—O(101) | 2.347(7) |
| Dy(1)—O(103) | 2.353(8) |
| Dy(1)—O(8) | 2.391(9) |
| Dy(1)—O(11) | 2.396(7) |

Since the Ga$_8$Dy$_2$ complex crystallizes in the space group P-1, the two Dy$^{3+}$ ions are symmetry related by an inversion center and are situated 7.23 Å apart, such that any through-space interactions are likely negligible. As with Ga$_4$Ln(shi)$_4$, the closest C—H oscillator resides on the nearest carbon of a bridging benzoate and is 4.51 Å apart from the nearest Dy$^{3+}$ ion. This distance is slightly longer than the 4.37 Å observed for Ga$_4$Dy(shi)$_4$.

Photophysical Properties
Ga$_4$Ln(shi)$_4$ Complexes

Figure 8:
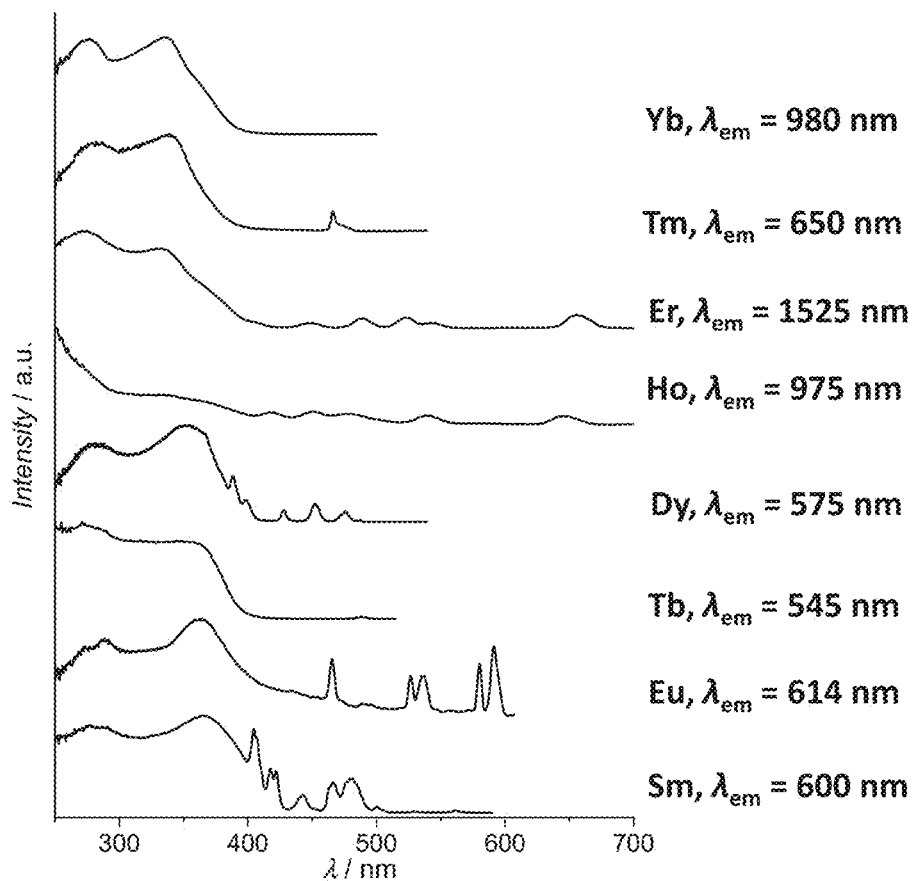
FIG. 8 is a graph illustrating the excitation spectra of the solid state Ga$_4$Ln(shi)$_4$ complexes.

All synthesized complexes (excluding Ga$_4$Gd(shi)$_4$) of the Ga$_4$Ln(shi)$_4$ series showed the ability to emit characteristic visible (Ga$_4$Tm(shi)$_4$, Ga$_4$Dy(shi)$_4$, Ga$_4$Tb(shi)$_4$, Ga$_4$Sm(shi)$_4$, Ga$_4$Eu(shi)$_4$) and/or near-infrared luminescence (Ga$_4$Dy(shi)$_4$, Ga$_4$Yb(shi)$_4$, Ga$_4$Ho(shi)$_4$, Ga$_4$Er(shi)$_4$, Ga$_4$Sm(shi)$_4$). For each of these metallacrowns, the bands observed in both the solution absorption (FIG. 5) and solid state diffuse reflectance (FIG. 6) spectra match well with those observed in the excitation spectra of the different Ga$_4$Ln(shi)$_4$ complexes (FIG. 8). This indicates that the excitation light is absorbed by the chromophoric H$_3$shi ligands and that the corresponding energy is being transferred to the luminescent lanthanides. Thus, this metallacrown design is able to provide an antenna effect for these different lanthanide cations emitting in the visible and in the NIR.

Figure 7:
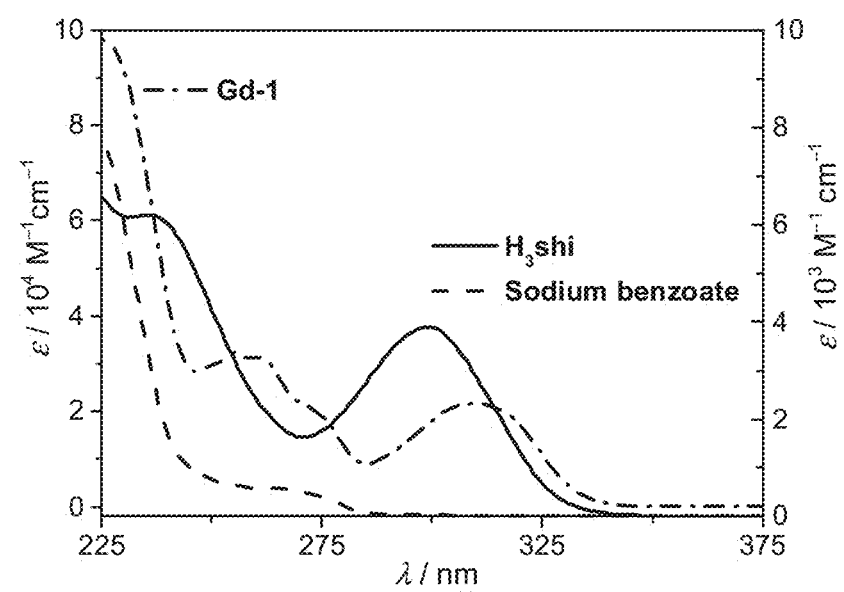
FIG. 7 is a graph depicting the absorption spectra of Ga$_4$Gd(shi)$_4$, H$_3$shi and sodium benzoate in methanol at 298 K.

The Gd$^{3+}$ derivative in this series is a useful probe to assess the ligand-centered photophysical properties of these metallacrowns, since this cation is not expected to exhibit Ln$^{3+}$ luminescence as the energy of the triplet state of the shi$^{3-}$ ligand is hypothesized to be too low to transfer to the accepting Gd$^{3+}$ level. The absorption spectrum of Ga$_4$Gd exhibits two major features attributed to the ligand-based π→π* transitions with the lower energy absorption band located at 310 nm (corresponding to an energy of ca. 32,250 cm$^{-1}$, FIG. 7). This band is red-shifted by 11 nm compared to the one of the ligand H$_3$shi, which exhibits low-energy π→π* absorption centered at 299 nm (FIG. 7); sodium benzoate does not show absorption bands below ca. 285 nm (FIG. 7).

Figure 5:
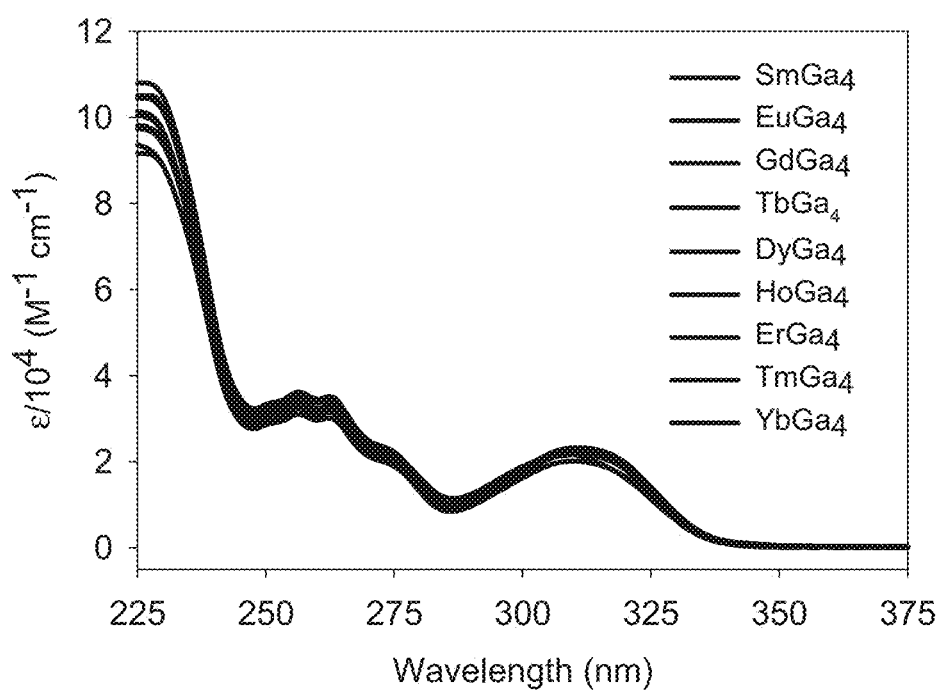
FIG. 5 is a graph of the UV-Vis absorption spectra for the Ga$_4$Ln(shi)$_4$ complexes in methanol at 298 K.
Figure 6A:
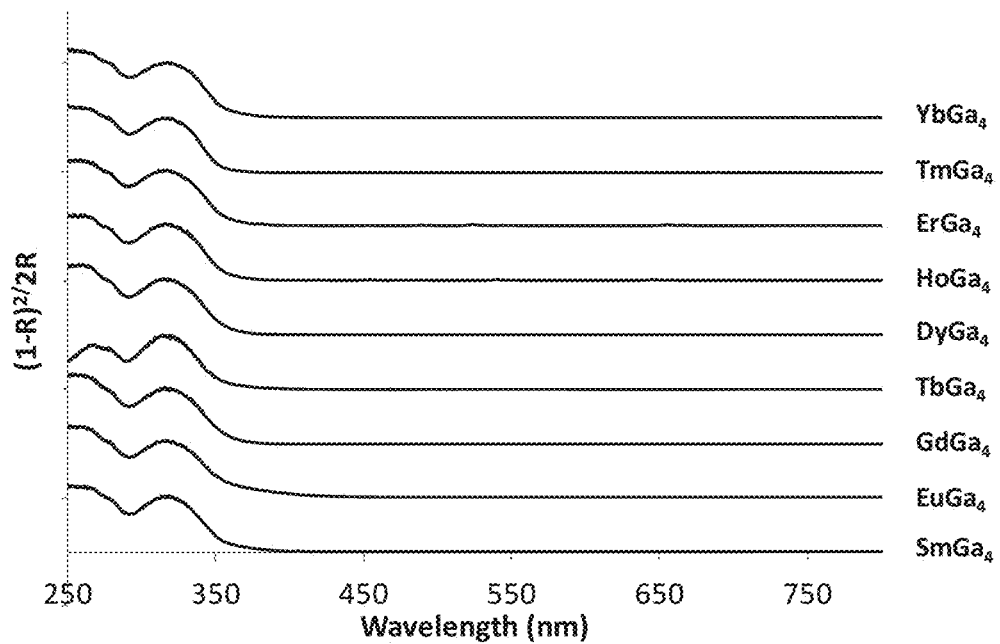
FIG. 6A is a graph of the diffuse reflectance spectra for the solid state Ga$_4$Ln(shi)$_4$ complexes presented as Kubelka-Munk function vs. wavelength
Figure 6B:
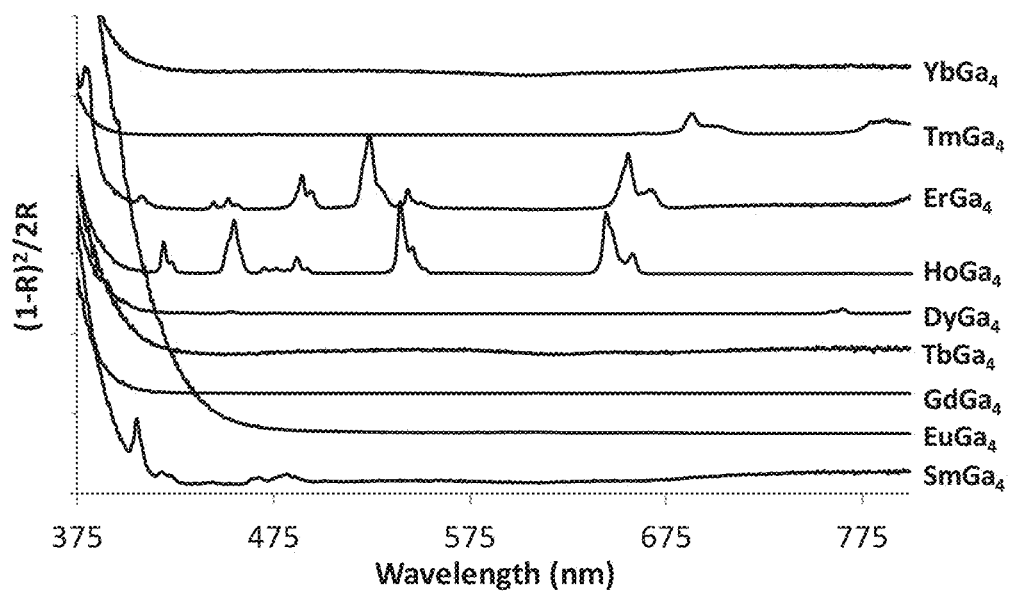
FIG. 6B is an enlargement of the spectra in the range 375-780 nm.

All of the synthesized Ga$_4$Ln(shi)$_4$ complexes exhibit similar solution absorption spectra indicating that the nature of the lanthanide ion does not affect the electronic properties of the resulting complex (FIG. 5). In diffuse reflectance spectra of solid state Ga$_4$Ln(shi)$_4$ complexes (FIG. 6) apart from broad-band ligand-centered transitions sharp characteristic bands which can be attributed to the corresponding f-f transitions of Sm$^{3+}$, Ho$^{3+}$, Er$^{3+}$ and Tm$^{3+}$ are observed. Moreover, in the case of Ga$_4$Eu(shi)$_4$, ligand-to-metal charge transfer (LMCT) can be detected as an extension of the band to longer wavelengths (FIG. 6). The LMCT cannot be observed in the solution UV-Vis spectra due to its low molar absorption coefficient.

Figure 9:
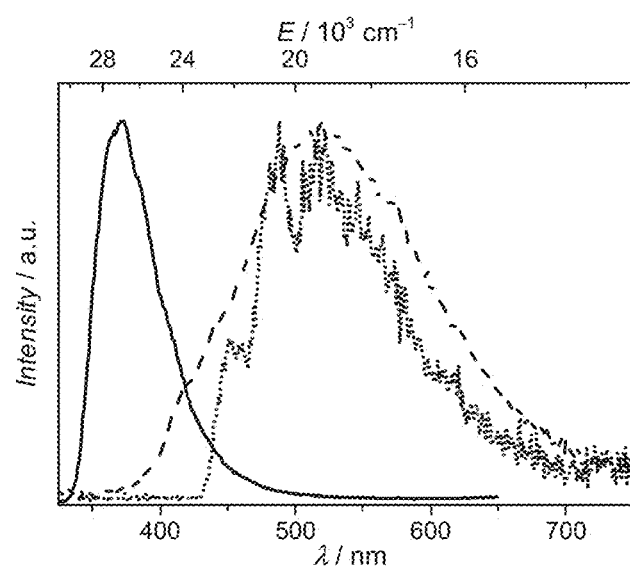
FIG. 9 is a graph showing the ligand-based photophysical properties of Ga$_4$Gd(shi)$_4$, including the luminescence under excitation at 325 nm at 298 K in methanol solution (black) and solid state (dotted line), and phosphorescence in solid state (grey; $\lambda_{ex}$=350 nm, 77 K, 200 μs delay after the excitation flash)

Under excitation at 325 nm in solution (CH$_3$OH) at room temperature, Ga$_4$Gd(shi)$_4$ exhibits fluorescence arising from its chromophoric moieties at 367 nm (ca. 27,250 cm$^{-1}$, FIG. 9), which is 5000 cm$^{-1}$ lower in energy than the absorption band. Phosphorescence can be observed by recording the signal emitted from Ga$_4$Gd(shi)$_4$ in time-resolved mode in the solid state at 77K upon excitation at 350 nm and using a 200 μS delay after the excitation flash (FIG. 9). The 0-0 component of this band represents the energy level of the ligand's triplet state (T$_1$=22,170 cm$^{-1}$, 451 nm) which is attributed to the energy level responsible for the main contribution of the transfer to the Ln$^{3+}$. The T$_1$ level is sufficiently high in energy to populate the excited states of a wide range of visible and NIR-emitting Ln$^{3+}$. However, the energy difference (αE) between the donating triplet state of the reported metallacrowns and the main accepting emitting levels of Tm$^{3+}$ ($^1$G$_4$, 21 350 cm$^{-1}$), Tb$^{3+}$ ($^5$D$_4$, 20 400 cm$^{-1}$) and Dy$^{3+}$ ($^4$F$_{9/2}$, 21 100 cm$^{-1}$) is relatively small (<2 000 cm$^{-1}$), suggesting that back energy transfer processes from the luminescent lanthanide to the chromophoric ligand is possible as discussed below.

Emission spectra of Ga$_4$Tm(shi)$_4$, Ga$_4$Sm(shi)$_4$, Ga$_4$Eu(shi)$_4$, Ga$_4$Dy(shi)$_4$, Ga$_4$Tb(shi)$_4$, Ga$_4$Ho(shi)$_4$, Ga$_4$Yb(shi)$_4$, and Ga$_4$Er(shi)$_4$ were collected in solid state samples (FIG. 10), and in MeOH or MeOD solutions when possible (not shown). The results of this photophysical study are summarized in Table 3 below. Excitation spectra recorded on solid samples (FIG. 8) and on solutions (not shown) are dominated by broad-bands up to 380-400 nm due to the ligand-based transitions. In addition, sharp bands which can be assigned to f-f transitions were observed for the Ga$_4$Tm(shi)$_4$, Ga$_4$Sm(shi)$_4$, Ga$_4$Eu(shi)$_4$, Ga$_4$Dy(shi)$_4$, Ga$_4$Tb(shi)$_4$, Ga$_4$Ho(shi)$_4$, and Ga$_4$Er(shi)$_4$ samples recorded in the solid state, though they are less pronounced for the Ga$_4$Tb(shi)$_4$ with a lower relative intensity. These f-f transitions were not observed in solution.

One parameter that can be obtained from the recording of luminescence lifetimes is the hydration number q. Estimations have been developed by comparing lifetimes in deuterated and protic solvents, and are summarized in Table 3.

The hydration number was calculated to be between ca. 0.7 and 1.2, indicating that the $Ln^{3+}$ is coordinated to one molecule of solvent. This non-zero q value is particularly detrimental for the intensity of the luminescence (and to the corresponding quantum yield values) of NIR-emitting lanthanides since the overtones of high-energy vibrations of the solvent molecules create a route for non-radiative deactivation. These results are in accordance with the previous discussion of the crystal structure of $Ga_4Ln$: it is possible that the void space between bridging benzoate molecules may be occupied by a solvent molecule.

visible characteristic bands originating from the $^1G_4$ energy level and terminating on the $^3H_6$ and $^3F_4$ ground state levels. The signal of the former transition overlaps with a broad organic emission arising from the chromophoric ligand as the result of a not complete ligand to lanthanide energy transfer or back transfer. The NIR bands of $Tm^{3+}$ could not be observed. Furthermore, no characteristic $Tm^{3+}$ visible or NIR emission was observed from this sample in solution, which could be explained by an increased role of quenching processes.

TABLE 3

Photophysical data for $Ga_4Ln(shi)_4$ MC complexes.

| MC | State/Solvent | $\Delta E$ $(cm^{-1})^a$ | $\tau_{obs}$ (µs) | q | $Q_{Ln}^L$ (%) (visible) | $Q_{Ln}^L$ (%) (NIR) |
|---|---|---|---|---|---|---|
| $Ga_4Sm(shi)_4$ | Solid | 4 270 | 148(1) | $0.8^b$ | 2.46(8) | 0.450(4) |
| | $CD_3OD$ | | 255(1) | | 2.33(5) | 0.298(1) |
| | $CH_3OH$ | | 27.6(1) | | 0.252(1) | $2.65(6) \cdot 10^{-2}$ |
| $Ga_4Eu(shi)_4$ | Solid | 4 910 | 242(7): 79% 43(2): 21% | | $1.59(4) \cdot 10^{-2}$ | — |
| $Ga_4Tb(shi)_4$ | Solid | 1 770 | 1080(10) | $1.2^c$ | 34.7(1) | — |
| | $CD_3OD$ | | 1960(10) | $0.9^d$ | 28.6(1) | — |
| | $CH_3OH$ | | 1510(10) | | 23.7(3) | — |
| $Ga_4Dy(shi)_4$ | Solid | 1 070 | 21.2(2) | $0.7^e$ | 2.10(1) | 0.21(1) |
| | $CD_3OD$ | | 25.5(7) | | 0.78(1) | $6.0(1) \cdot 10^{-2}$ |
| | $CH_3OH$ | | 12.0(1) | | 0.38(1) | $2.4(1) \cdot 10^{-2}$ |
| $Ga_4Ho(shi)_4$ | Solid | 6 670 | 0.029(1) | | — | $2.0(2) \cdot 10^{-3}$ |
| $Ga_4Er(shi)_4$ | Solid | 15 470 | 6.75(3) | | — | $4.4(1) \cdot 10^{-2}$ |
| | $CD_3OD$ | | 1.74(1) | | — | $4.5(3) \cdot 10^{-2}$ |
| $Ga_4Tm(shi)_4$ | Solid | 820 | 1.47(1) | | $0.02(1)^f$ | — |
| $Ga_4Yb(shi)_4$ | Solid | 11 870 | 55.7(3) | | — | 5.88(2) |
| | $CD_3OD$ | | 36.6(1) | $0.7^g$ | — | 4.29(1) |
| | $CH_3OH$ | | 2.06(4) | | — | 0.26(1) |

$^a \Delta E(T - E^{Ln})$ is the energy gap between the ligand triplet state ($T_1 = 22\,170\, cm^{-1}$) and $Ln^{3+}$ emissive state: $E^{Sm}\, (^4G_{5/2}) = 17\,900\, cm^{-1}$, $E^{Eu}\, (^5D_0) = 17\,260\, cm^{-1}$, $E^{Tb}\, (^5D_4) = 20\,400\, cm^{-1}$, $E^{Dy}\, (^4F_{9/2}) = 21\,100\, cm^{-1}$, $E^{Ho}\, (^5F_5) = 15\,500\, cm^{-1}$, $E^{Er}\, (^4I_{13/2}) = 6\,700\, cm^{-1}$, $E^{Tm}\, (^1G_4) = 21\,350\, cm^{-1}$, $E^{Yb}\, (^2F_{5/2}) = 10\,300\, cm^{-1}$.
$^b q_{Sm} = 2 \times [25.4 \times (k_{CH_3OH} - k_{CD_3OD}) - 0.37]$ in µs.
$^c q_{Tb} = 8.2 \times (k_{CH_3OH} - k_{CD_3OD})$ in ms.
$^d q_{Tb} = 10.0 \times (k_{CH_3OH} - k_{CD_3OD} - 0.06)$ in ms.
$^e q_{Dy} = 2 \times [21.1 \times (k_{CH_3OH} - k_{CD_3OD}) - 0.6]$ in µs.
$^f$ Quantum yield of Tm-centered transitions after the subtraction of the ligand-based signal; the total quantum yield of $Ga_4Tm(shi)_4$ is 0.12(1)%.
$^g q_{Yb} = 2 \times (k_{CH_3OH} - k_{CD_3OD} - 0.1)$ in µs.

The $Ga_4Eu(shi)_4$ complex exhibited transitions between the $^5D_0$ emitting state to $^7F_{0-4}$ states between 575 nm and 725 nm (FIG. 10) in the solid state, which are typical for $Eu^{3+}$ compounds. The relatively small quantum yield and short luminescent lifetime observed (Table 3) are likely due to the quenching effect of LMCT states.

Figure 10:
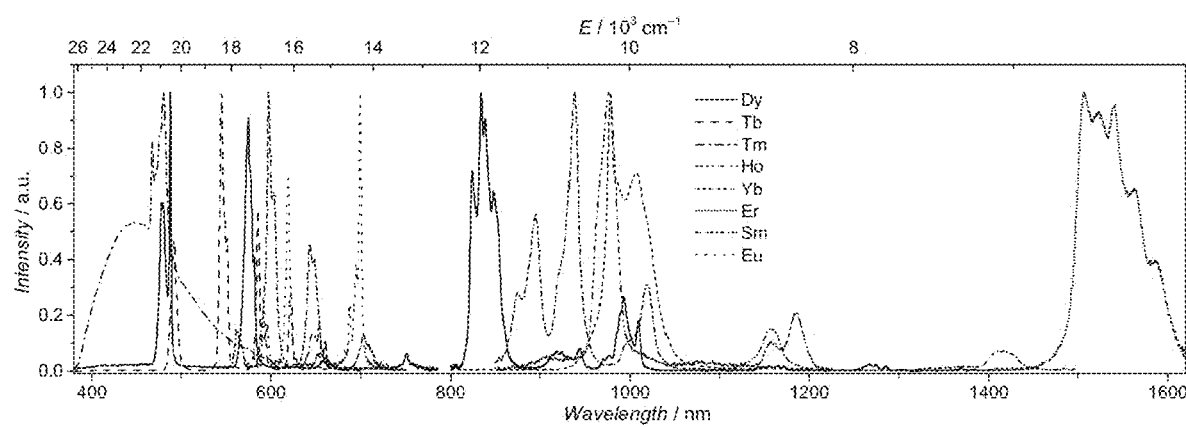
FIG. 10 is a graph depicting emission spectra of solid state Ga$_4$Ln(shi)$_4$ complexes under ligand excitation at 350 nm at 298 K.

The main emitting state for $Sm^{3+}$ ion is $^4G_{5/2}$, which is only slightly higher in energy than the $^5D_0$ state for $Eu^{3+}$. In both the solid state and in solution characteristic $Sm^{3+}$ emission arising from $^4G_{5/2} \rightarrow {}^6H_J$ (J=5/2, 7/2, 9/2 and 11/2) transitions in the visible between 550 nm and 750 nm and $^4G_{5/2} \rightarrow {}^6F_J$ (J=1/2–11/2) transitions in the NIR (>800 nm) ranges in clearly observed (FIG. 10). The quantum yields for the visible emission in solution (2.33% in $CD_3OD$) and in the solid state (2.46%) are modest; as quantum yields up to 11% have been reported. However, the lifetime in $CD_3OD$ (255 µs) is quite long. Furthermore, the NIR emission corresponding to $^4G_{5/2} \rightarrow {}^6F_J$ (J=1/2–11/2) transitions (FIG. 10) are intense enough to obtain quantum yields in both the solid state and in solution (Table 3), which is rare.

The observation of an emission signal arising from $Tm^{3+}$ in molecular complexes that are formed with organic ligands is highly rare. The emission spectrum obtained for $Ga_4Tm(shi)_4$ (FIG. 10) recorded on a solid state sample shows two The emission spectrum of $Ga_4Dy(shi)_4$ recorded on solids-state samples (FIG. 10) exhibits a number of sharp bands across the visible and NIR regions, originating from electronic transitions between the excited $^4F_{9/2}$ energy level and the $^6H_J$ (J=15/2–5/2) and $^6F_J$ (J=7/2–1/2) ground state levels. In solution, a residual emission signal from the organic ligands was also observed, indicating an incomplete energy transfer to $Dy^{3+}$ or more efficient back energy transfer. Quantum yields recorded for $Ga_4Dy(shi)_4$ in the visible and the NIR are reported in Table 3. This result is believed to be the first quantitative report of NIR emission arising from $Dy^{3+}$.

Relatively strong emission bands resulting from transitions between the $^5D_4$ level and terminating at the $^7F_J$ (J=6–0) ground states were observed for $Ga_4Tb(shi)_4$ (FIG. 10), with a quantum yield of 34.7% in the solid state.

The desirable NIR emission from $Ho^{3+}$ is extremely rare in systems containing organic lanthanide sensitizers. The NIR emission arising from $Ga_4Ho(shi)_4$ was observed at 965-990 nm and is due to the $^5F_5 \rightarrow {}^5I_7$ transition and at 1160-1190 nm originating from the $^5I_6 \rightarrow {}^5I_8$ transition. The quantum yield for $Ga_4Ho(shi)_4$ in the solid-state ($2.0(2) \cdot 10^{-3}$%) is the first quantitative value reported. Emission signal in the visible was not observed, nor was it possible to collect an emission spectrum in protic solvents.

A $Yb^{3+}$ emission signal was observed with an apparent maximum at 980 nm for $Ga_4Yb(shi)_4$ and is attributed to the $^2F_{5/2} \rightarrow ^2F_{7/2}$ transition. The relatively shorter distance between the $Ln^{3+}$ and C—H oscillators in comparison to other, previously reported $Zn_{16}Ln$ metallacrowns, is expected to result in additional deactivation by quenching through these oscillators. Moreover, in solution an additional source of quenching has been identified through the coordination of a solvent molecule due to the insufficient protection of $Ln^{3+}$. Nevertheless, the quantum yield value that was measured for $Ga_4Yb(shi)_4$ in the solid state (5.88 (2)%) is over 1.5 fold higher than any other comparable reported quantum yields for $Yb^{3+}$ complexes with organic ligands containing C—H bonds. However, in solution, quantum yields are in the range of average values for other $Yb^{3+}$ complexes and are significantly lower than those measured in the solid state. These results can be partially explained by the non-zero value of q where the deactivation from the solvent will take a higher importance. From these observations, it can be concluded that the intrinsic sensitization efficiency is relatively high for this system, as demonstrated by the high quantum yields in the solid state.

For the $Er^{3+}$ complex $Ga_4Er(shi)_4$, the typical long wavelength emission is observed at ca. 1500-1600 nm originating from the $^4I_{13/2} \rightarrow ^4I_{15/2}$ transition. The quantum yield of this transition in the solid state is the same within experimental error as the value observed for the previously reported $Zn_{16}Er$ metallacrown complexes, $4.4(1) \cdot 10^{-2}\%$ versus $4.2(1) \cdot 10^{-2}\%$. This difference increases when the measurements are performed in deuterated solvent with the respective values of $4.5(3) \cdot 10^{-2}\%$ versus $3.60(6) \cdot 10^{-2}\%$. It is believed that these values are among the highest ever reported.

$Ga_8Ln_2(shi)_8$ Complexes

Figure 11:
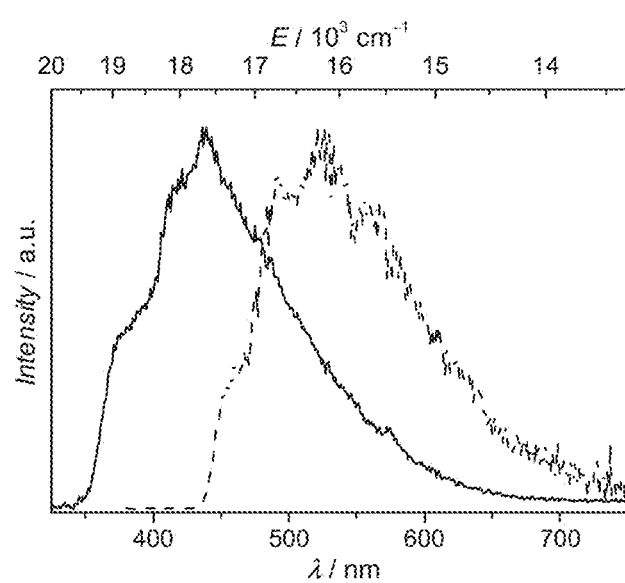
FIG. 11 is a graph depicting the ligand-based photophysical properties of the solid state Ga$_8$Gd$_2$(shi)$_8$, including the luminescence (black line, $\lambda_{ex}$=320 nm, 298 K) and phosphorescence (dotted line; $\lambda_{ex}$=350 nm, 77 K, 100 μs delay after the excitation flash)

Since the $Ga_8Ln_2(shi)_8$ dimer compounds were insoluble in all solvents, the solid state photophysical data alone were collected. As with the $Ga_4Gd(shi)_4$ compound, the $Ga_8Gd_2(shi)_8$ complex may be used to examine the ligand-based photophysical properties. At room temperature in the solid state, under 310 nm excitation, $Ga_8Gd_2(shi)_8$ exhibits broadband ligand-centered luminescence in the range 350-650 nm with a maximum at 440 nm (22 727 $cm^{-1}$, FIG. 11). The solid state ligand phosphorescence was obtained at 77 K using an excitation wavelength of 350 nm and a 100 μs delay (FIG. 11). The profile of the phosphorescence is similar to that of $Ga_4Gd(shi)_4$ (FIG. 9), which was expected, since both compounds are formed by the same framework ligand, $H_3shi$. The 0-0 transition was determined to be located at 455 nm, or 21 978 $cm^{-1}$. This triplet state energy is slightly lower than that of the $Ga_4Gd(shi)_4$ compound (22 170 $cm^{-1}$), but still is sufficiently high in energy to sensitize visible ($Dy^{3+}$, $Tb^{3+}$, $Sm^{3+}$) and/or NIR emitting ($Dy^{3+}$, $Sm^{3+}$, $Ho^{3+}$, $Yb^{3+}$, $Pr^{3+}$, $Nd^{3+}$, $Er^{3+}$) lanthanides.

Figure 12:
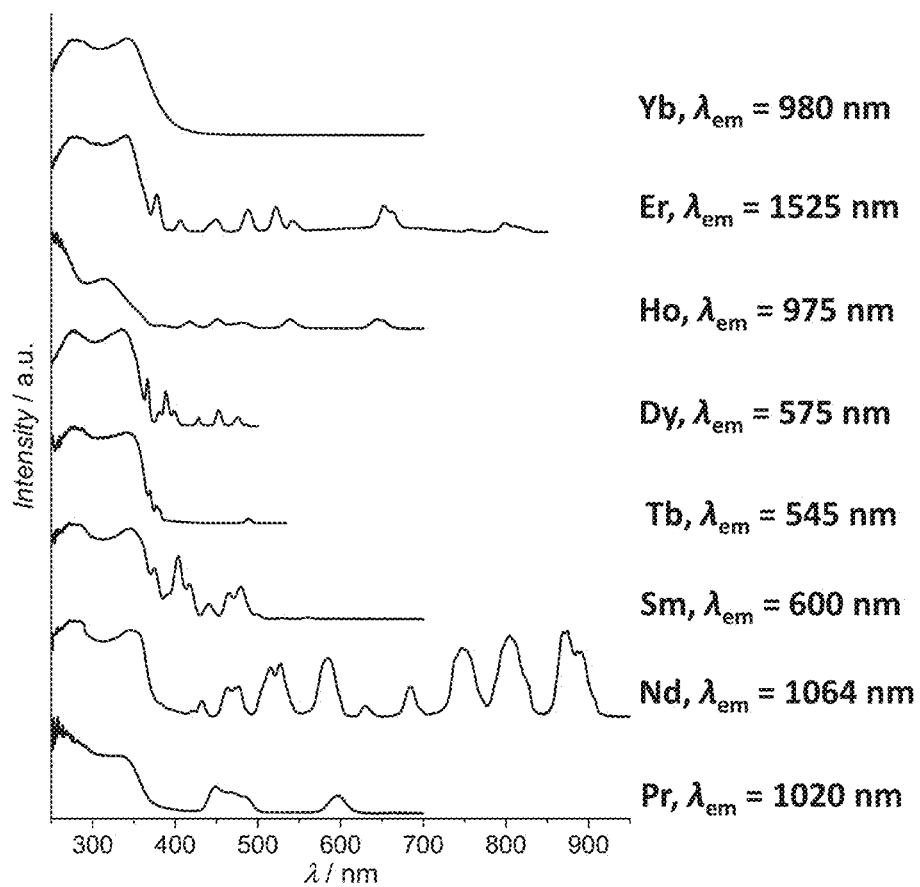
FIG. 12 is a graph depicting the excitation spectra of the solid state Ga$_8$Ln$_2$(shi)$_8$ complexes at 298K.

The excitation spectra of $Ga_8Ln_2(shi)_8$ MCs exhibit profiles similar to the ones observed for the $Ga_4Ln(shi)_4$ complexes (FIG. 8): broad ligand-centered bands up to 350-400 nm and sharp characteristic f-f transitions in the case of $Pr^{3+}$, $Nd^{3+}$, $Sm^{3+}$, $Tb^{3+}$, $Dy^{3+}$, $Ho^{3+}$ and $Er^{3+}$ MCs (FIG. 12). It is noted that for $Ga_8Nd_2(shi)_8$ MC the intensity of f-f transitions is comparable with the ligand-centered transitions (FIG. 12).

Figure 13:
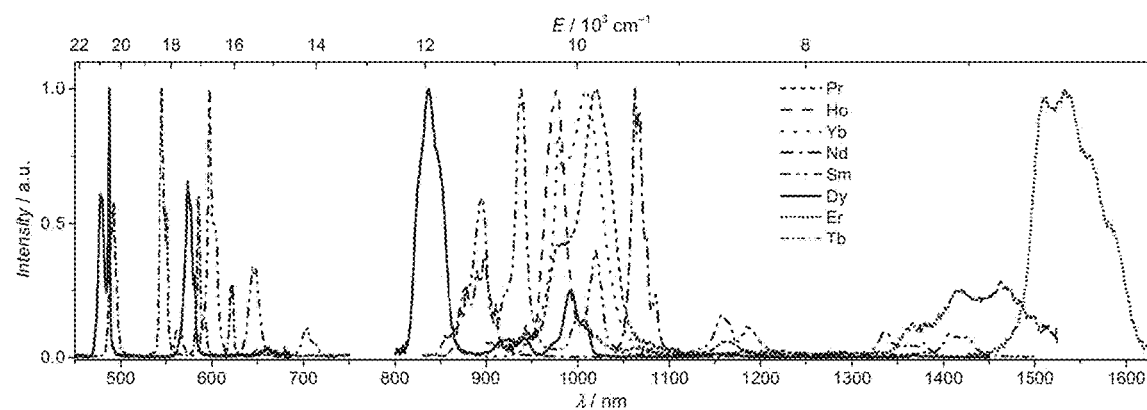
FIG. 13 is a graph depicting emission spectra of the solid state Ga$_8$Ln$_2$(shi)$_8$ under ligand excitation at 350 nm at 298 K.

Using an excitation wavelength of 350 nm, both visible and NIR emission arising from f-f transitions of different lanthanide ions can be observed (FIG. 13). Quantitative parameters are summarized in Table 4. In general, quantum yields are lower for $Ga_8Ln_2(shi)_8$ MCs compared to $Ga_4Ln$ $(shi)_4(shi)_8$ (Table 3) except for $Ho^{3+}$ analogues which quantum yield is increased by 1.65 times reaching $3.3(1) \cdot 10^{-3}\%$.

TABLE 4

Photophysical data for $Ga_8Ln_2(shi)_8$ MC complexes.

| MC | $\lambda_{em}$/nm | $\tau_{obs}$/μs $^a$ | $Q_{Ln}^L$ (%) (visible) | $Q_{Ln}^L$ (%) (NIR) |
|---|---|---|---|---|
| $Ga_8Pr_2(shi)_8$ | 1020 | 0.901(6) | — | $9.3(1) \cdot 10^{-3}$ |
| $Ga_8Nd_2(shi)_8$ | 1064 | 2.46(1) | — | 0.99(2) |
| $Ga_8Sm_2(shi)_8$ | 597 | 117(1) | 2.09(5) | 0.269(3) |
| $Ga_8Tb_2(shi)_8$ | 545 | 1410(1) | 31.2(2) | — |
| $Ga_8Dy_2(shi)_8$ | 575 | 15.0(1) | 0.85(1) | $7.5(1) \cdot 10^{-2}$ |
| $Ga_8Ho_2(shi)_8$ | 978 | 0.032(1) | — | $3.3(1) \cdot 10^{-3}$ |
| $Ga_8Er_2(shi)_8$ | 1525 | 5.23(2) | — | $5.7(1) \cdot 10^{-3}$ |
| $Ga_8Yb_2(shi)_8$ | 980 | 30.5(1) | — | 2.43(6) |

Figures 14A, 14B:
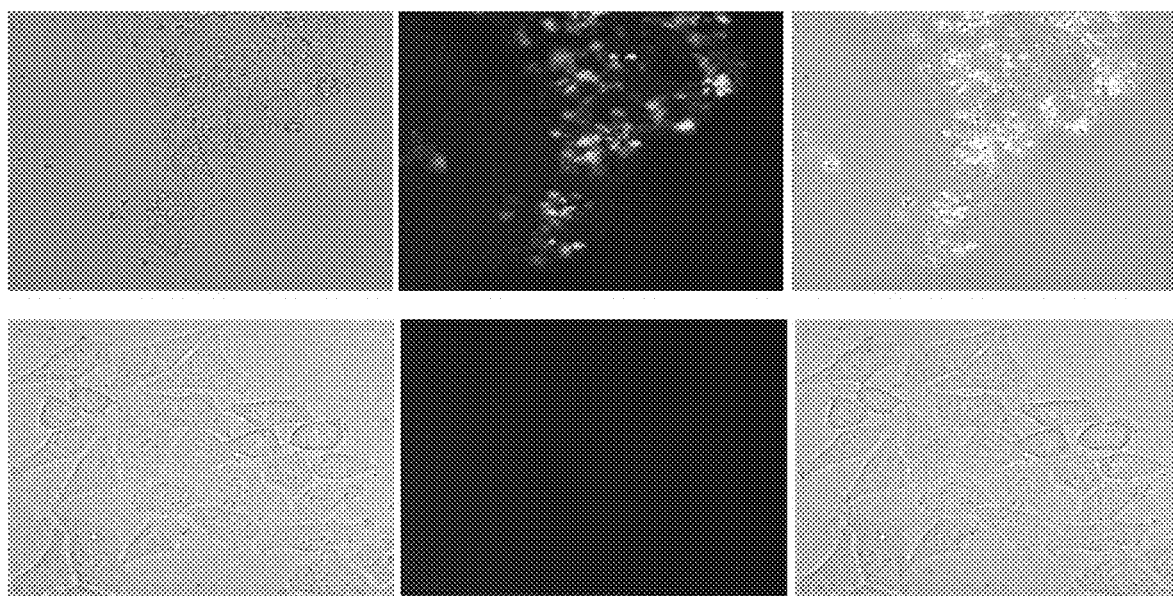
FIGS. 14A and B are microscope images of Ga$_8$Yb$_2$(shi)$_8$ when incubated with HeLa cells for 3 hours at 10 μM concentration, where
FIG. 14B represents a control where no MC was added upon incubation.

HeLa (Human Epithelial Ovarian Carcinoma) cell line obtained from ATCC (Molsheim, France) was cultured in Dulbecco's modified Eagle's medium (DMEM) supplemented with 10% heat-inactivated fetal bovine serum (FBS), 1% of 100× non-essential aminoacid solution, 1% of L-glutamine (GlutaMAX) and 1% of streptomycin/penycilin antibiotics. Cells were seeded in a 8-well Lab Tek Chamber coverglass (Nunc, Dutsher S.A., Brumath, France) at a density of $6 \times 10^4$ cells/well and cultured at 37° C. in 5% humidified $CO_2$ atmosphere. After 24 hours, cell culture media was removed, and cells were washed twice with OPTIMEM (room temperature) and incubated with a solution of the $Ga_8Yb_2(shi)_8$ complex in OPTIMEM media supplemented with 2% of FBS at 37° C. in 5% $CO_2$ atmosphere during 3 hours. Prior to epifluorescent imaging the cells were washed twice with OPTIMEM (room temperature) in order to remove any non-specifically bound $Ga_8Yb_2(shi)_8$ complex. The cells were observed with a Zeiss Axio Observer Z1 fluorescence inverted microscope (Zeiss, Le Pecq, France) equipped with an EMCCD Evolve 512 (Roper Scientific) photometric camera. The light source, Zeiss HXP 120, was combined with the following filter cubes: 377 nm band pass 50 nm filter for the excitation and long pass filter 805 nm for $Yb^{3+}$ emission in the NIR range. The FIGS. 14A and B are microscope images of the $Ga_8Yb_2(shi)_8$ when incubated with the HeLa cells. FIG. 14A represents the brightfield (left), the NIR emission (center), and the merged (right) images, and FIG. 14B represents a control where no MC was added upon incubation.

The data presented in Example 1 presents a modular metallacrown platform that is highly efficient for the sensitization of visible and near-infrared lanthanide metal ions. Highly luminescent $Ga_4Ln(shi)_4$ coordination compounds can be obtained by the four-component self-assembly synthetic process disclosed herein. The size of the lanthanide has an impact on the formation of the complex; as the assembly for $Ln^{3+}$ ions larger than $Sm^{3+}$ could not be obtained. On the other hand, dimeric MCs $Ga_8Ln_2$ could be assembled for large lanthanides like $Nd^{3+}$ and $Pr^{3+}$. The electronic structure of the metallacrowns is remarkable in its ability to sensitize several lanthanide cations emitting in the visible ($Eu^{3+}$, $Tb^{3+}$, $Tm^{3+}$) and in the near-infrared ($Ho^{3+}$, $Er^{3+}$, $Yb^{3+}$, $Pr^{3+}$, $Nd^{3+}$) or in both ($Sm^{3+}$ and $Dy^{3+}$). The sensitization of a wide range of NIR emitting lanthanide cations opens new possibilities for multiplex bioanalytical experiments.

Unlike the $LnZn_{16}L_{16}$ sandwich complexes, the protection of the lanthanide cation against non-radiative deactivations in $Ga_4Ln(shi)_4$ MCs is not optimized but could be further improved. The design of these structures localizes the lanthanide cation at the center of the assembly, with the goal of precluding luminescence quenching arising from interactions with high-energy vibrations of surrounding molecules. However, a pocket between the bridging carboxylates provides a space for coordination of solvent molecules, as confirmed by the q values estimated from luminescence lifetimes in protic and deuterated solvents (Table 3). Nevertheless, the efficient sensitization ability of the $H_3shi$ chromophores leads to highly luminescent visible and NIR $Ln^{3+}$ emitters. It is believed that the results in this example are the highest quantum yield values for $Yb^{3+}$ and $Er^{3+}$ complexes containing organic ligands Additionally, the $Ga_8Ln_2(shi)_8$ dimer compounds exhibited lower quantum yields and luminescent lifetimes than the $Ga_4Ln(shi)_4$ monomer complexes, reflecting the versatility of the disclosed systems and the possibility of easy tuning of photophysical properties.

The simplicity and synthetic reliability of the 12-MC-4 system provides ample opportunity to modulate structural features such as the framework and bridging ligands, in order to tune both the photophysical parameters and physical properties such as solution integrity, solubility, and add platforms for further coupling reactions. Such modifications include the extension of the aromatic ring of shi to naphthanoic hydroxamic acid, or the replacement of a CH unit with a nitrogen into the aromatic ring as shown in isonicotinic hydroxamic acid. Other modifications on shi and isophthalic acid include the addition of ethynyl, azido, isothiocyano, isocyano, and malimido substituents onto the aromatic rings.

As an example of utilization of copper-catalyzed alkyne azide cycloaddition, an ethynylsalicylhydroxamic acid derivative was coupled to an azido biotin derivative, both of which were prepared according to literature procedures. The reaction of these complexes in water:terf-butanol solution in the presence of cupric sulfate, sodium ascorbate (NaAsc, a reductant), and tri(benzyltriazylpropyl)amine (TBTA, a chelating agent) resulted in the formation of the coupled compound according to the following scheme:

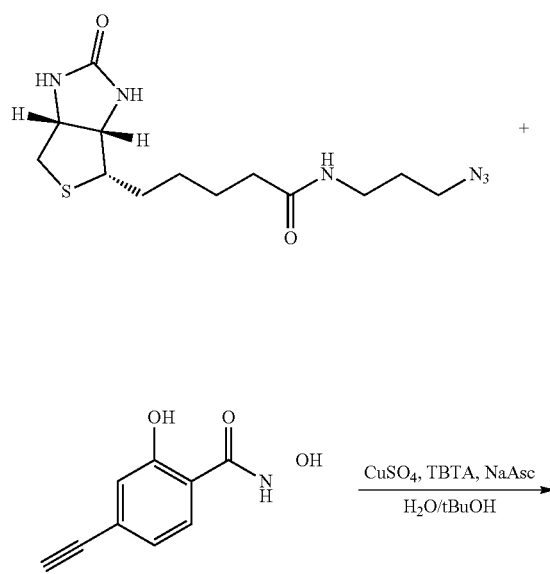

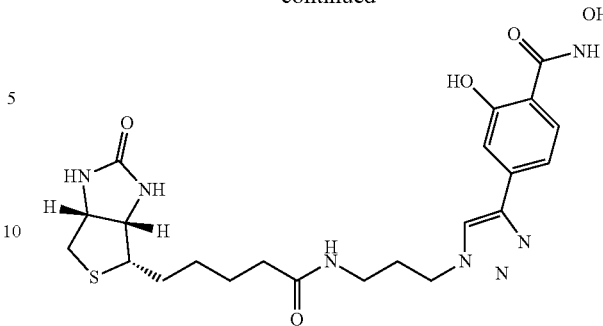

Figure 31:
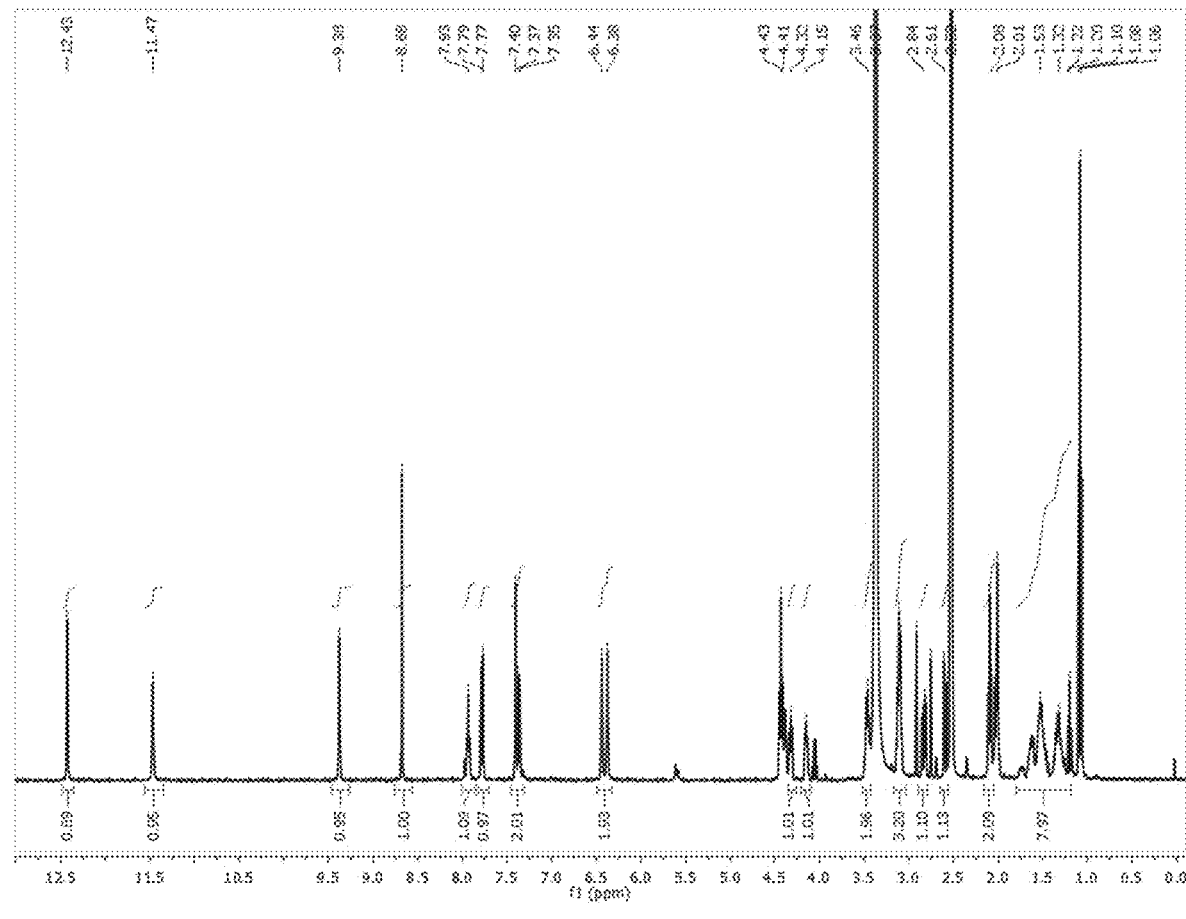
FIG. 31 is the $^1$H-NMR of the biotin-eshi coupled molecule (example 1)
Figure 32:
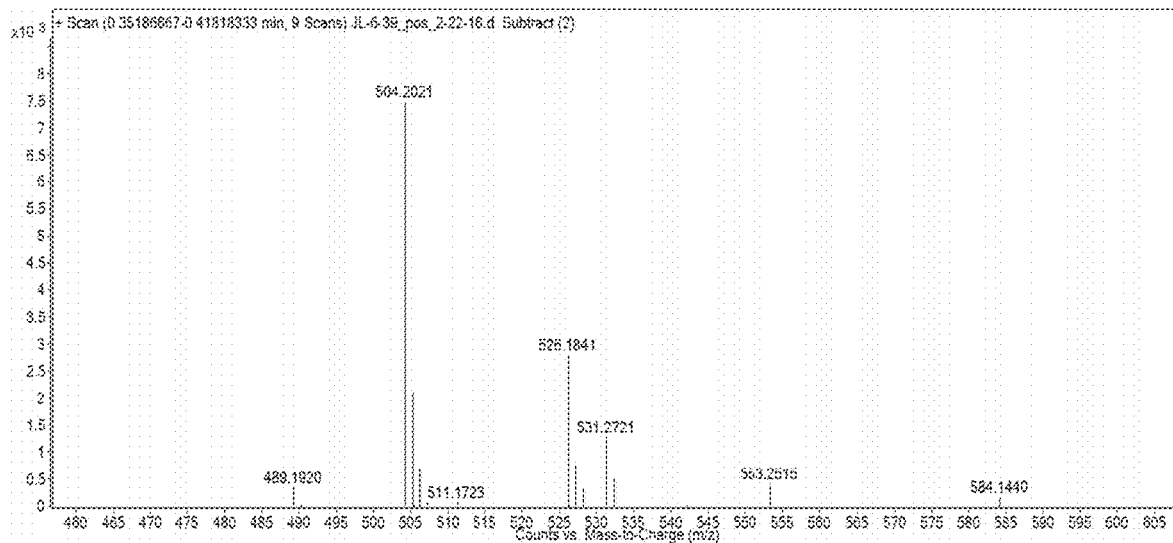
FIG. 32 is the ESI-MS+ of the biotin-eshi coupled molecule (example 1): parent peak present at 504.2; sodium adduct at 526.2.

ESI-MS and 1H-NMR of this compound are provided in FIGS. 31 and 32. This procedure should be adaptable for use directly on metallacrown complexes containing ethynyl or azido functionalization.

Example 2

Preparation of Complexes $Ga_4Ln(shi)_6$ $H_3shi$ (153.1 mg, 1.0 mmol), $Ln(NO_3)_3.xH_2O$ (0.25 mmol), and $Ga(NO_3)_3.xH_2O$ (255.7 mg, 1.0 mmol) were dissolved in 10 mL methanol. Pyridine (2 mL) and acetic acid (0.1 mL) were added and the mixture was stirred for 2 hours. The solution was filtered and kept undisturbed. X-ray quality crystals form after one day.

[$GdGa_4(shi)_4(H_2shi)_2(C_5H_5N)_4(NO_3)$].$(C_5H_5N)_2$ ($Ga_4Gd$ (shi)$_6$). Yield: 131 mg (28%). ESI-MS, calc. for [M]$^-$, $C_{42}H_{26}N_6O_{18}GdGa_4$, 1338.8; found, 1337.9. Anal. Calcd for $GdGa_4C_{72}H_{58}N_{13}O_{21}$: C, 46.06; H, 3.11; N, 9.70. Found: C, 46.02; H, 3.07; N, 9.33.

[$TbGa_4(shi)_4(H_2shi)_2(C_5H_5N)_4(NO_3)$].$(C_5H_5N)_2$ ($Ga_4Tb$ (shi)$_6$). Yield: 153 mg (33%). ESI-MS, calc. for [M]$^-$, $C_{42}H_{26}N_6O_{18}GdGa_4$, 1340.5; found, 1339.8. Anal. Calcd for $TbGa_4C_{72}H_{58}N_{13}O_{21}$: C, 46.02; H, 3.11; N, 9.69. Found: C, 46.31; H, 3.20; N, 9.64.

[$DyGa_4(shi)_4(H_2shi)_2(C_5H_5N)_4(NO_3)$].$(C_5H_5N)_2$ ($Ga_4Dy$ (shi)$_6$). Yield: 151 mg (32%). ESI-MS, calc. for [M]$^-$, $C_{42}H_{26}N_6O_{18}DyGa_4$, 1344.1; found, 1343.9. Anal. Calcd for $DyGa_4C_{72}H_{58}N_{13}O_{21}$: C, 45.93; H, 3.11; N, 9.67. Found: C, 46.22; H, 3.17; N, 9.49.

[$HoGa_4(shi)_4(H_2shi)_2(C_5H_5N)_4(NO_3)$].$(C_5H_5N)_2$ ($Ga_4Ho$ (shi)$_6$). Yield: 147 mg (31%). ESI-MS, calc. for [M]$^-$, $C_{42}H_{26}N_6O_{18}HoGa_4$, 1346.5; found, 1346.8. Anal. Calcd for $HoGa_4C_{72}H_{58}N_{13}O_{21}$: C, 45.87; H, 3.10; N, 9.66. Found: C, 46.10; H, 3.13; N, 9.48.

[$ErGa_4(shi)_4(H_2shi)_2(C_5H_5N)_5$].$(NO_3)$.$(C_5H_5N)$ ($Ga_4Er$ (shi)$_6$). Yield: 127 mg (27%). ESI-MS, calc. for [M]$^-$, $C_{42}H_{26}N_6O_{18}ErGa_4$, 1348.9; found, 1347.9. Anal. Calcd for $ErGa_4C_{72}H_{58}N_{13}O_{21}$: C, 45.82; H, 3.10; N, 9.65. Found: C, 45.68; H, 3.37; N, 9.35.

[$TmGa_4(shi)_4(H_2shi)_2(C_5H_5N)_5$].$(NO_3)$.$(C_5H_5N)$ ($Ga_4Tm(shi)_6$). Yield: 166 mg (35%). ESI-MS, calc. for [M]$^-$, $C_{42}H_{26}N_6O_{18}ErGa_4$, 1350.5; found, 1350.8. Anal. Calcd for $TmGa_4C_{72}H_{58}N_{13}O_{21}$: C, 45.78; H, 3.09; N, 9.64. Found: C, 45.48; H, 3.35; N, 9.26.

[$YbGa_4(shi)_4(H_2shi)_2(C_5H_5N)_5$].$(NO_3)$.$(C_5H_5N)_2$ ($Ga_4Yb(shi)_6$). Yield: 114 mg (24%). ESI-MS, calc. for [M]$^-$, $C_{42}H_{26}N_6O_{18}ErGa_4$, 1354.6; found, 1353.8. Anal. Calcd for $YbGa_4C_{72}H_{58}N_{13}O_{21}$: C, 45.68; H, 3.09; N, 9.62. Found: C, 45.85; H, 3.30; N, 9.31.

Figure 2A:
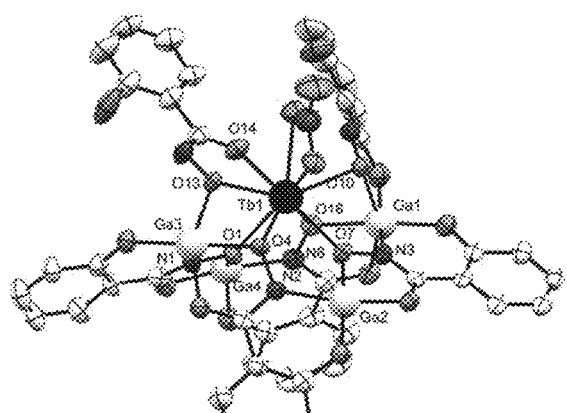
FIGS. 2A and 2B are the X-ray crystal structures of Ga$_4$Tb(shi)$_6$ and its Ln$^{3+}$[12-MC$_{Ga}^{III}$$_{N(shi)}$-4] core.
Figure 2B:
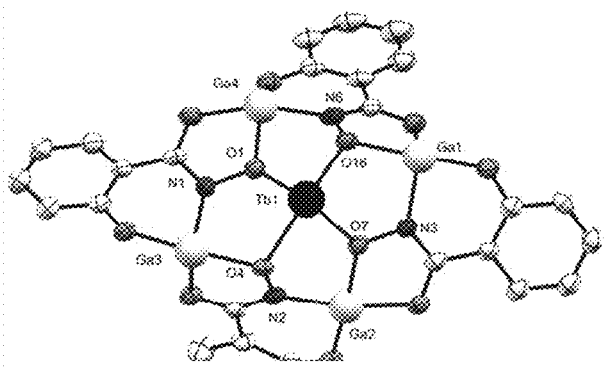

The X-ray crystal structure of the representative molecule $Ga_4Tb(shi)_6$ is shown in FIG. 2A. The complex crystallizes in the triclinic space group P1̄. Compounds $Ga_4Ln(shi)_6$ (Ln=$Gd^{3+}$, $Tb^{3+}$, $Dy^{3+}$, $Ho^{3+}$, $Er^{3+}$, $Tm^{3+}$, $Yb^{3+}$) contain a non-planar $Ln^{3+}$(12-$MC_{Ga}{}^{III}{}_{N(Shi)}$-4) core (shown in FIG. 2B for Tb-2). The central Ln ion is bridged to two gallium ions by two $H_2shi^-$ ligands and its coordination sphere is filled by a chelating nitrate.

Figure 15:
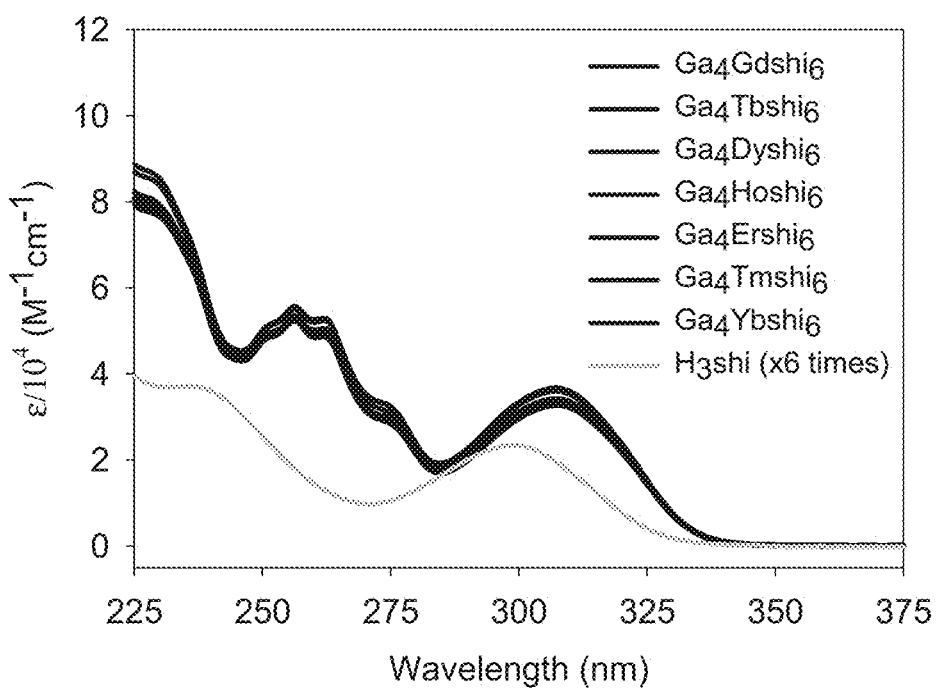
FIG. 15 is a graph depicting the UV/Vis absorption spectra of H$_3$shi and Ga$_4$Ln(shi)$_6$ molecules in methanol at 298 K.
Figure 16A:
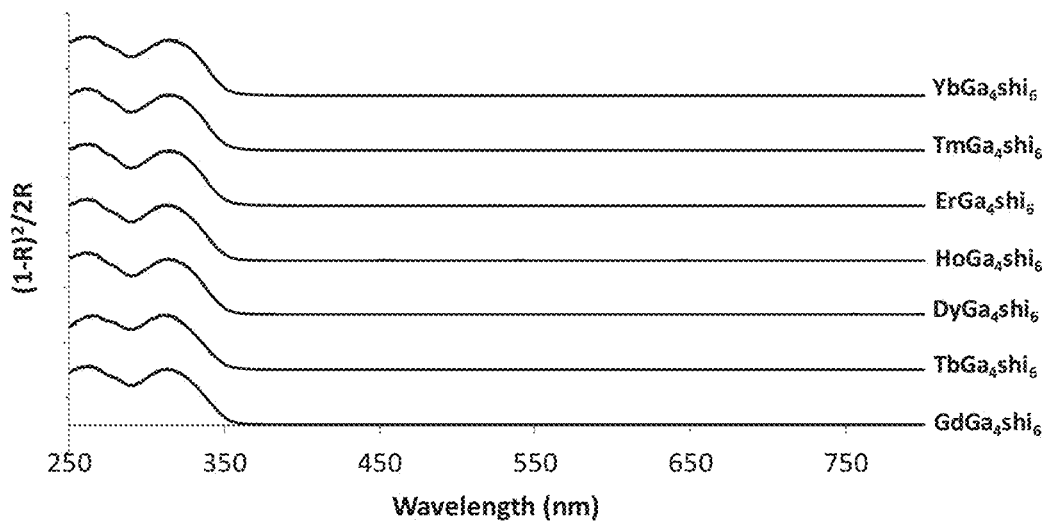
FIG. 16A is a graph depicting the diffuse reflectance spectra of solid state Ga$_4$Ln(shi)$_6$ complexes presented as Kubelka-Munk function vs. wavelength
Figure 16B:
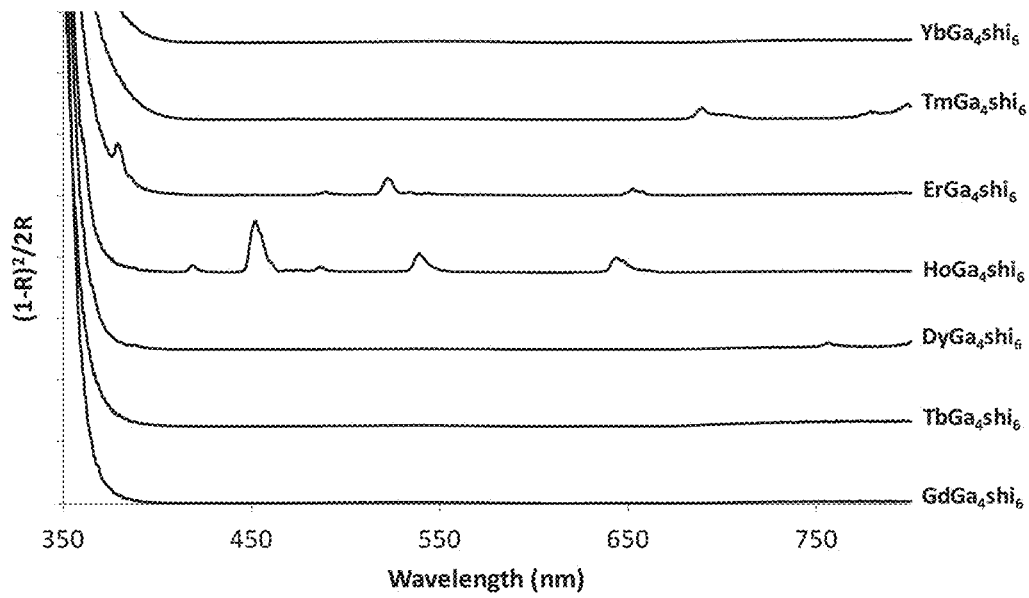
FIG. 16B is an enlargement of the spectra in the range 375-780 nm.
Figure 17:
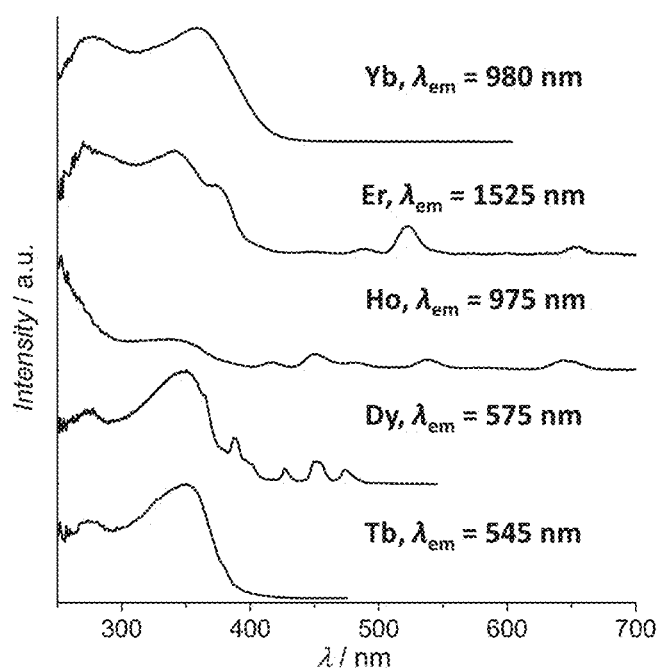
FIG. 17 is a graph depicting the excitation spectra of Ga$_4$Ln(shi)$_6$ complexes upon monitoring main emission transition of the corresponding lanthanide(III) ions.
Figure 18:
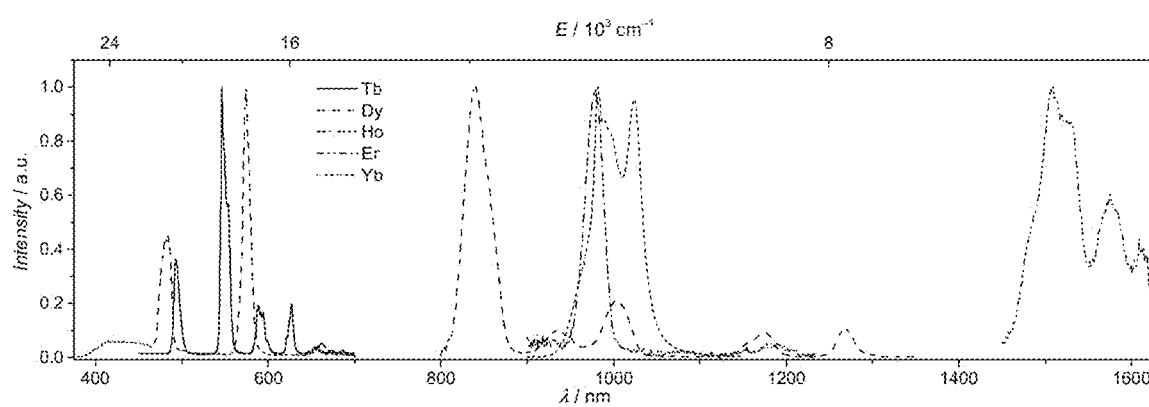
FIG. 18 is a graph depicting the emission spectra of Ga$_4$Ln(shi)$_6$ complexes upon ligand excitation.

The UV-Vis spectroscopy data for the $H_3shi$ and the $Ga_4Ln(shi)_6$ molecules in methanol solution are shown in FIG. 15, the diffuse reflectance spectra of the $Ga_4Ln(shi)_6$ molecules are shown in FIG. 16A, the excitation and emission spectra of $Ga_4Ln(shi)_6$ complexes are respectively shown in FIGS. 17 and 18.

Table 5 depicts the photophysical parameters of some of the solid state $Ga_4Ln(shi)_6$ molecules.

TABLE 5

Photophysical parameters of solid state $Ga_4Ln(shi)_6$

| Compound | $Q_{Ln}{}^L$/% | | $\tau/\mu s$ |
|---|---|---|---|
| | VIS | NIR | |
| $Ga_4Tbshi_6$ | 11.3(5) | | 509(7) |
| $Ga_4Dyshi_6$ | 0.308(8) (total) 0.222(6) (only Dy) | n.a. | 3.36(6) |
| $Ga_4Hoshi_6$ | | n.a. | 0.032(1) |
| $Ga_4Ershi_6$ | | $1.55(3) \cdot 10^{-3}$ | 0.220(3) |
| $Ga_4Ybshi_6$ | | 0.216(6) | 2.99(2) |

Example 3

Synthetic Procedure for [$LnGa_6(shi)_7(Hshi)(H_2shi)(C_6H_{16}N)_3(C_5H_5N)_2$]·$xH_2O$ [$Ga_6Ln(shi)_9$]

$Ga(NO_3)_3$·$xH_2O$ (273.8 mg, 1.0 mmol), and $Ln(NO_3)_3$·$xH_2O$ (0.1667 mmol) were dissolved in 10 mL of methanol. Separately, $H_3shi$ (229.8 mg, 1.5 mmol), triethylamine (0.62 mL, 4.5 mmol) and pyridine (10 mL) were mixed, then added to the metal salt solution, and was left to stir overnight. The solution was filtered and allowed to crystallize via diffusion of diethyl ether. Crystals were observed in 1-2 weeks.

[$PrGa_6(shi)_7(Hshi)(H_2shi)(C_6H_{16}N)_3(C_5H_5N)_2$]·$4H_2O$ [$Ga_6Pr(shi)_9$]: Yield: 116.5 mg (28%). Elemental Analysis for $PrGa_6C_{91}H_{105}N_{14}O_{31}$ (Calcd): 44.98%; C, (44.61); 4.28%; H, (4.32); 8.22%; N, (8.00).

[$NdGa_6(shi)_7(Hshi)(H_2shi)(C_6H_{16}N)_3(C_5H_5N)_2$]·$7H_2O$ [$Ga_6Nd(shi)_9$]: Yield: 68.1 mg (2%). ESI-MS for [M]$^-$ $NdGa_6C_{63}H_{41}N_9O_{27}$ (Calcd): 1917.2 (1914.7). Elemental Analysis for $NdGa_6C_{91}H_{111}N_{14}O_{34}$ (Calcd): 43.59%; C, (43.59); 4.30%; H, (4.46); 7.87%; N, (7.82).

[$SmGa_6(shi)_7(Hshi)(H_2shi)(C_6H_{16}N)_3(C_5H_5N)_2$]·$6H_2O$ [$Ga_6Sm(shi)_9$]: Yield: 134.2 mg (33%). ESI-MS for [M]$^-$ $SmGa_6C_{63}H_{41}N_9O_{27}$ (Calcd): 1925.3 (1924.76). Elemental Analysis for $SmGa_6C_{91}H_{109}N_{14}O_{33}$ (Calcd): 43.81%; C, (43.80); 4.32%; H, (4.40); 8.00%; N, (7.86).

[$TbGa_6(shi)_7(Hshi)(H_2shi)(C_6H_{16}N)_3(C_5H_5N)_2$] [$Ga_6Tb(shi)_9$]: Yield: 138.5 mg (36%). ESI-MS for [M]$^-$ $TbGa_6C_{63}H_{41}N_9O_{27}$ (Calcd): 1932.1 (1933.32). Elemental Analysis for $TbGa_6C_{91}H_{97}N_{14}O_{27}$ (Calcd): 45.43%; C, (45.62); 4.23%; H, (4.08); 8.19%; N, (8.18).

[$DyGa_6(shi)_7(Hshi)(H_2shi)(C_6H_{16}N)_3(C_5H_5N)$]·$6H_2O$ [$Ga_6Dy(shi)_9$]: Yield: 98.8 mg (24%). ESI-MS for [M]$^-$ $DyGa_6C_{63}H_{41}N_9O_{27}$ (Calcd): 1936.9 (1936.9). Elemental Analysis for $DyGa_6C_{91}H_{111}N_{14}O_{34}$ (Calcd): 42.48%; C, (42.53); 4.21%; H, (4.32); 7.60%; N, (7.50).

[$HoGa_6(shi)_7(Hshi)(H_2shi)(C_6H_{16}N)_3(C_5H_5N)_2$]·$8H_2O$ [$Ga_6Ho(shi)_9$]: Yield: 49.4 mg (12%). Elemental Analysis for $HoGa_6C_{91}H_{113}N_{14}O_{35}$ (Calcd): 42.63%; C, (42.93); 4.38%; H, (4.47); 7.64%; N, (7.70).

[$ErGa_6(shi)_7(Hshi)(H_2shi)(C_6H_{16}N)_3(C_5H_5N)_2$]·$6H_2O$ [$Ga_6Er(shi)_9$]: Yield: 40.8 mg (10%). ESI-MS for [M]$^-$ $SmGa_6C_{63}H_{41}N_9O_{27}$ (Calcd): 1941.0 (1939.7). Elemental Analysis for $ErGa_6C_{91}H_{109}N_{14}O_{33}$ (Calcd): 43.39%; C, (43.50); 4.36%; H, (4.37); 7.78%; N, (7.80).

[$YbGa_6(shi)_7(Hshi)(H_2shi)(C_6H_{16}N)_3(C_5H_5N)_2$]·$8H_2O$ [$Ga_6Yb(shi)_9$]: Yield: 102.5 mg (24%). ESI-MS for [M]$^-$ $YbGa_6C_{63}H_{41}N_9O_{27}$ (Calcd): 1947.0 (1946.7). Elemental Analysis for $YbGa_6C_{91}H_{113}N_{14}O_{35}$ (Calcd): 42.85%; C, (42.79); 4.18%; H, (4.46); 7.71%; N, (7.68).

Figure 19A:
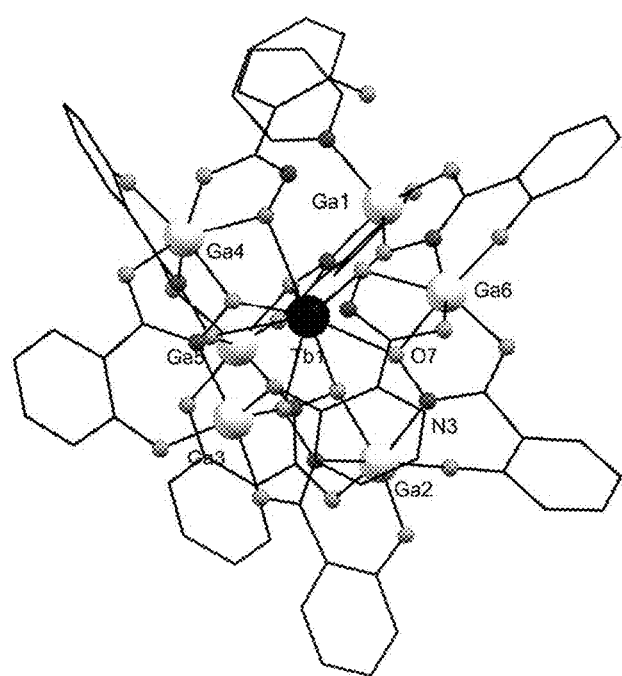
FIG. 19A is the crystal structure of Ga$_6$Dy(shi)$_9$.
Figure 19B:
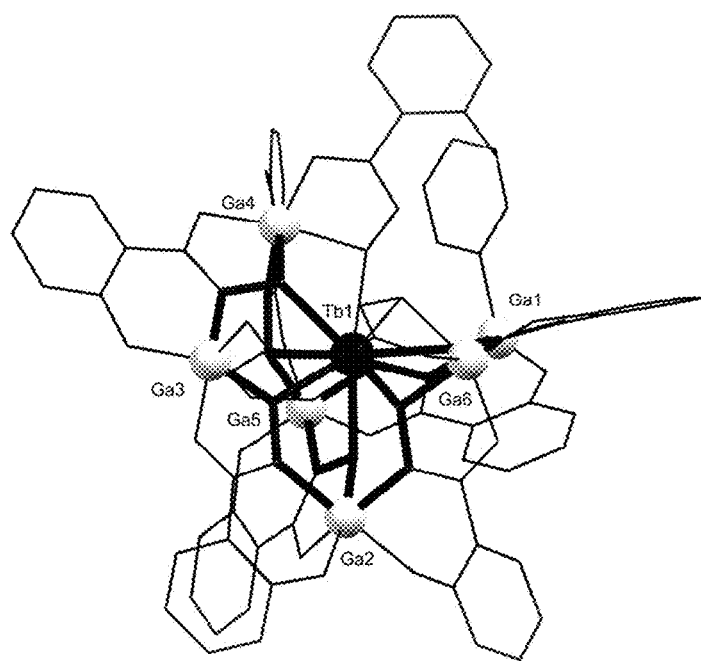
FIGS. 19B and 19C are representations of the two gallium 12-MC-4s of Ga$_6$Dy(shi)$_9$; one involves Ga1, Ga2, Ga3, and Ga6 (FIG. 19B); the other involves Ga1, Ga3, Ga4 and Ga5 (FIG. 19C)
Figure 19C:
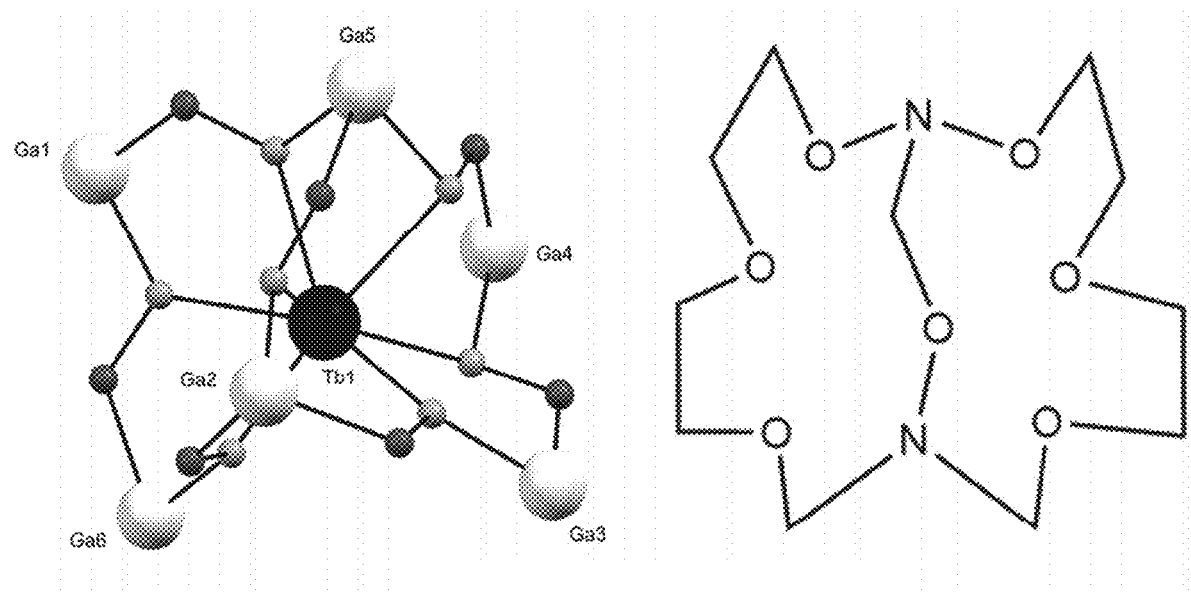

FIGS. 19A-C show a crystal structure of $Ga_6Tb(shi)_9$, which crystallizes in P$\bar{1}$. The central $Tb^{3+}$ ion is nine coordinate, binding to the oximate oxygens of nine $H_3shi$ ligands, with a geometry described as tricapped trigonal prism. Four of the gallium ions (Ga2, Ga4, Ga5, and Ga6) are in distorted octahedral environments with propeller confirmations; Ga2 and Ga4 are $\wedge$ while Ga5 and Ga6 are $\Delta$ chirality. The remaining gallium ions (Ga1 and Ga3) are five coordinate, with a geometry closer to square pyramidal, $\tau$=0.2525 and 0.2697 respectively.

Figure 20:
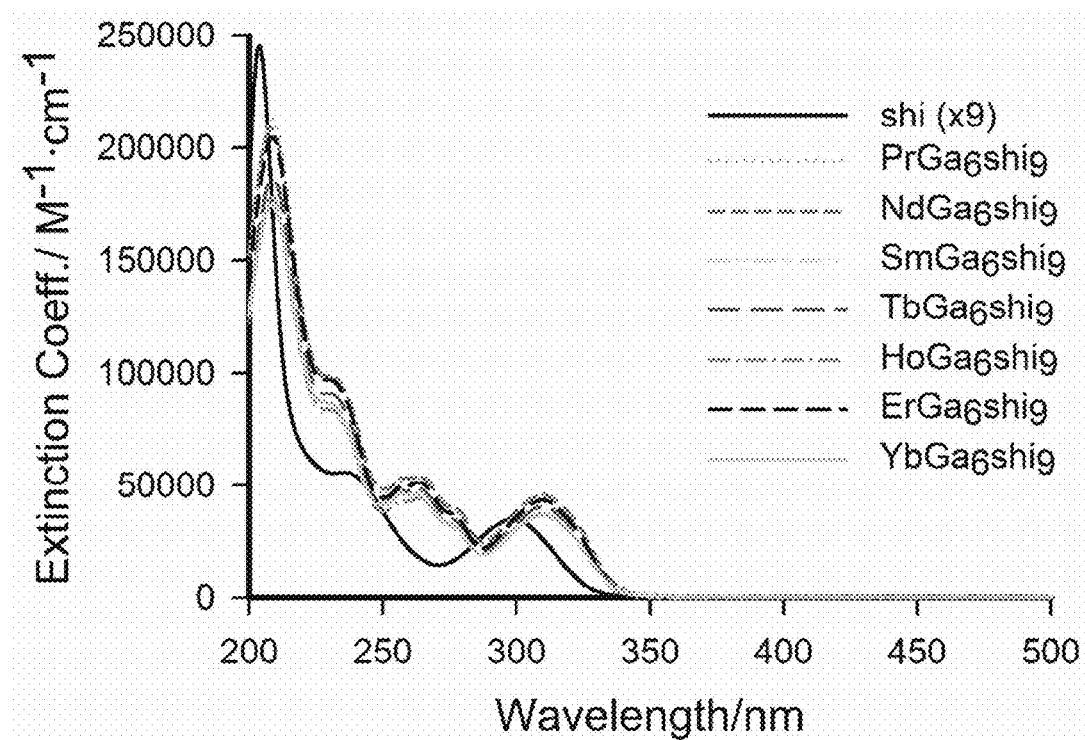
FIG. 20 is a graph depicting the UV/Vis absorption spectra of Ga$_6$Ln(shi)$_9$ (Ln=Tb, Sm, or Dy) molecules at 298 K.
Figure 21A:
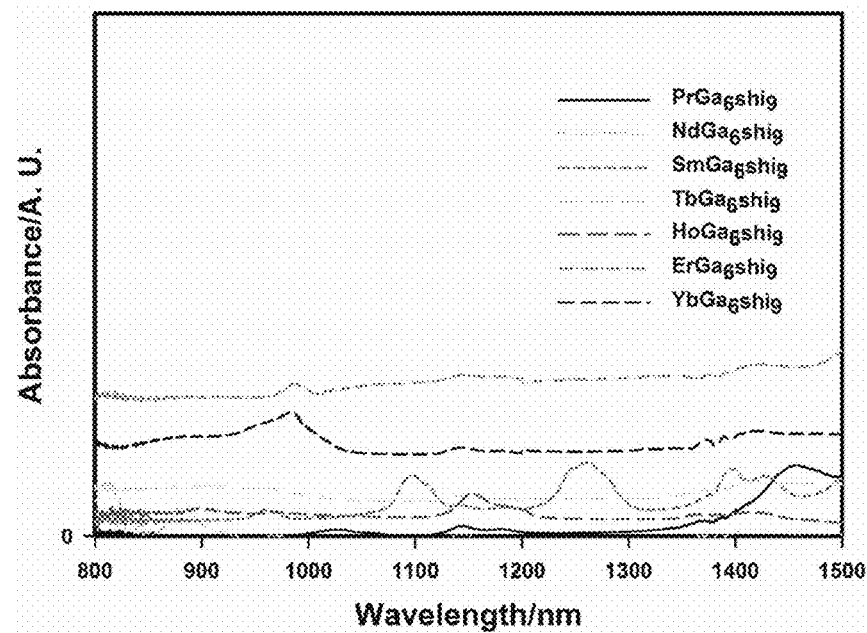
FIG. 21A is a graph depicting the diffuse reflectance spectra of Gd$_4$Ln(shi)$_9$ presented as Kubelka-Munk function vs. wavelength
Figure 21B:
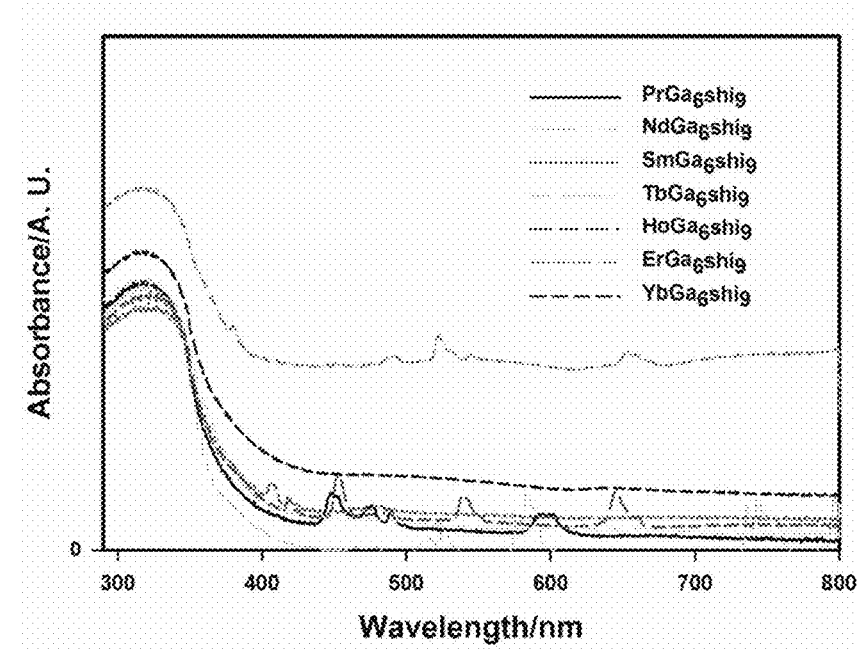
FIG. 21B is an enlargement of the spectra in the range 375-780 nm.
Figure 22:
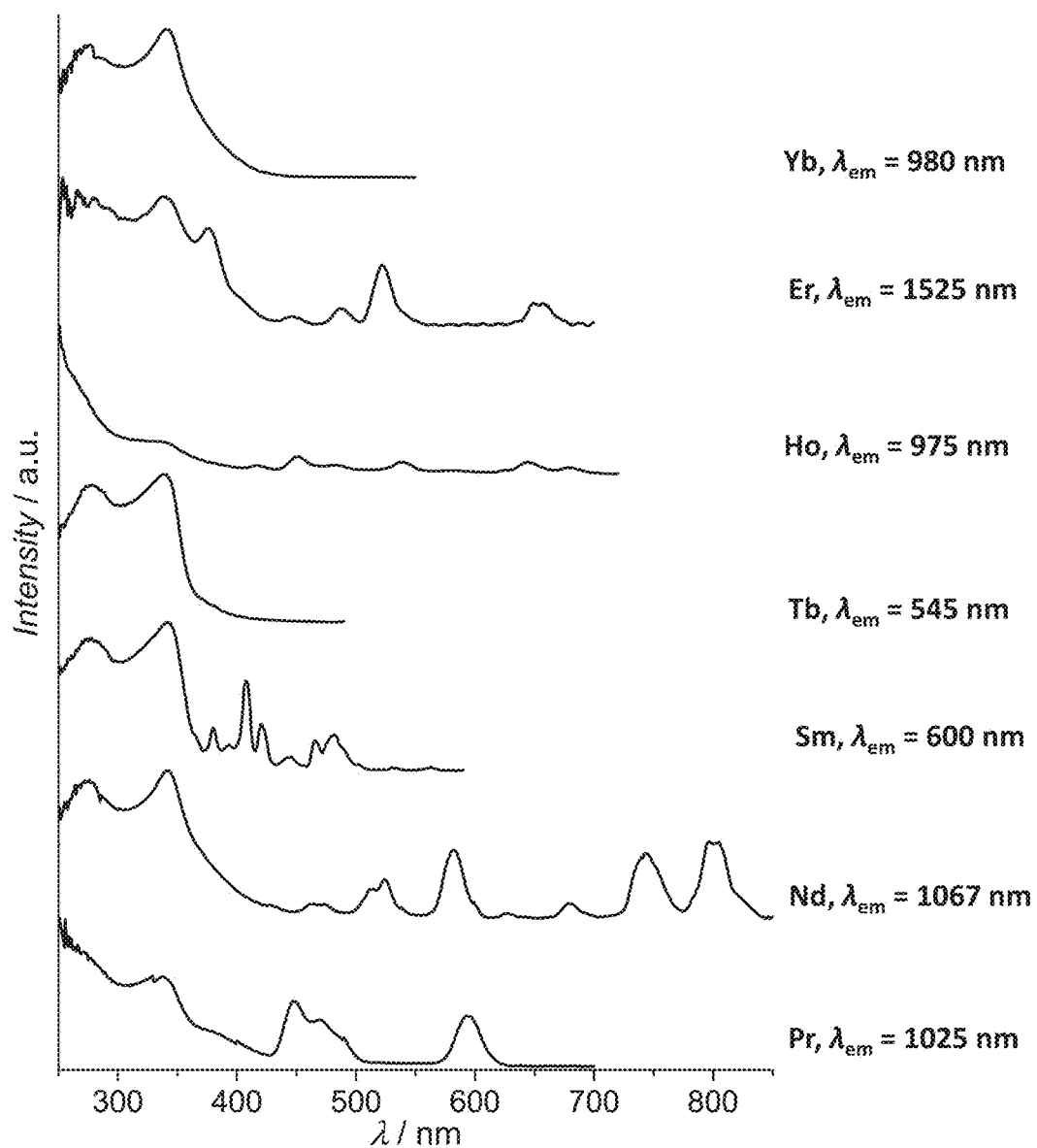
FIG. 22 is a graph depicting the excitation spectra of Ga$_4$Ln(shi)$_9$ complexes upon monitoring main emission transition of the corresponding lanthanide(III) ions.
Figure 23:
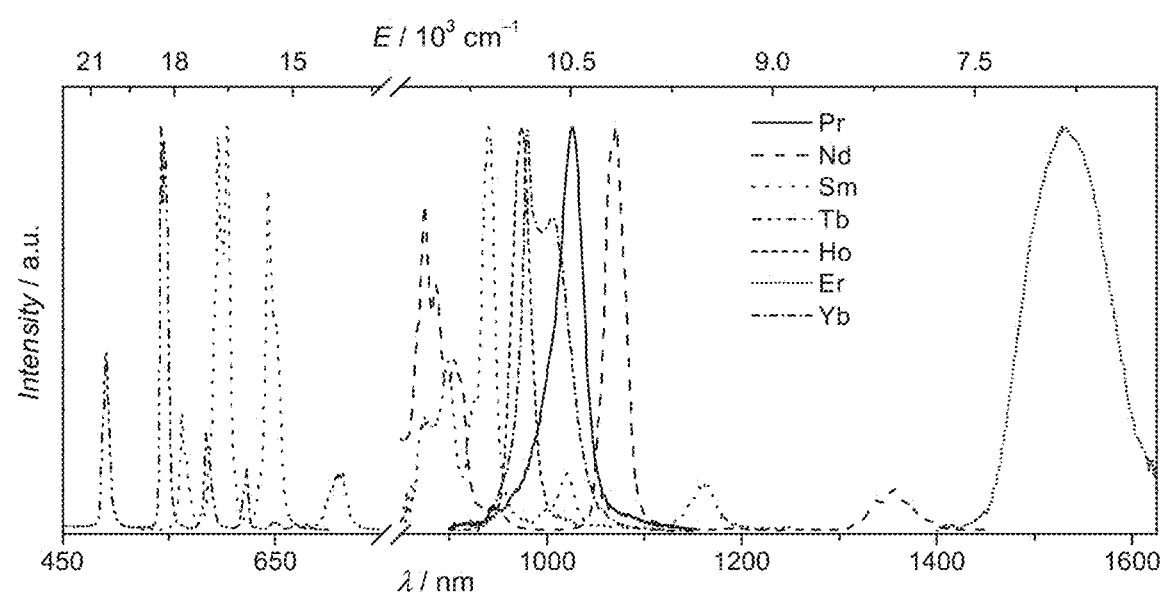
FIG. 23 is a graph depicting the emission spectra of Ga$_4$Ln(shi)$_9$ complexes upon ligand excitation.
Figure 24:
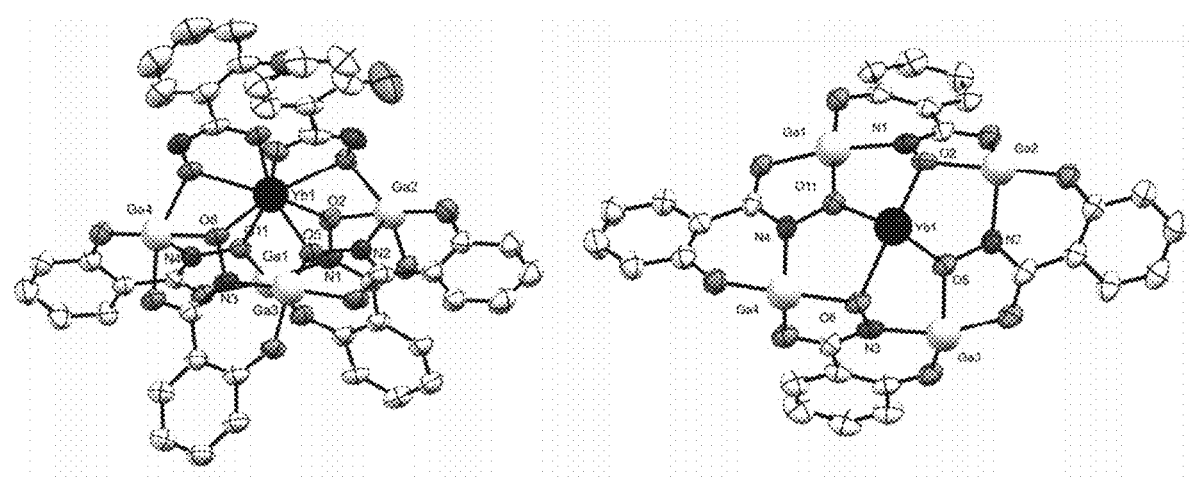
FIG. 24 is the crystal structure of Ga$_4$Yb(shi)$_6$ with no bound nitrate.
Figure 25:
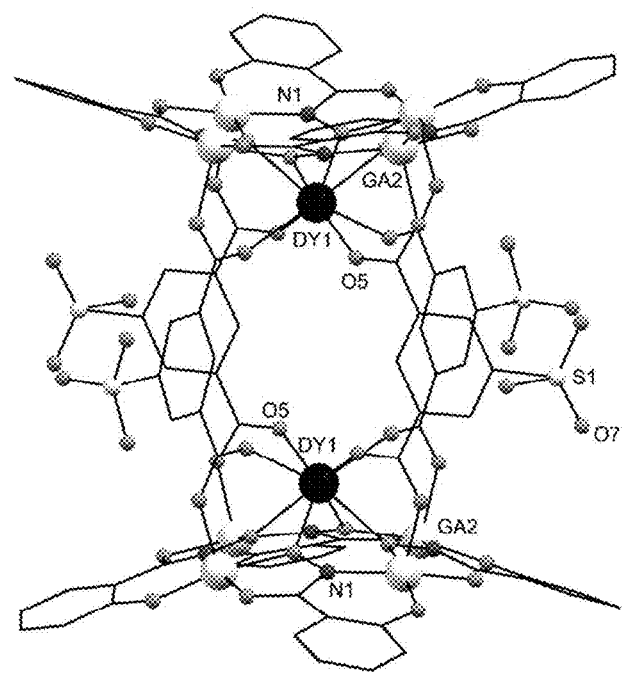
FIG. 25 is the crystal structure of Ga$_8$Dy$_2$(shi)$_8$ with the SO$_3$ groups on isophthalates.
Figure 26:
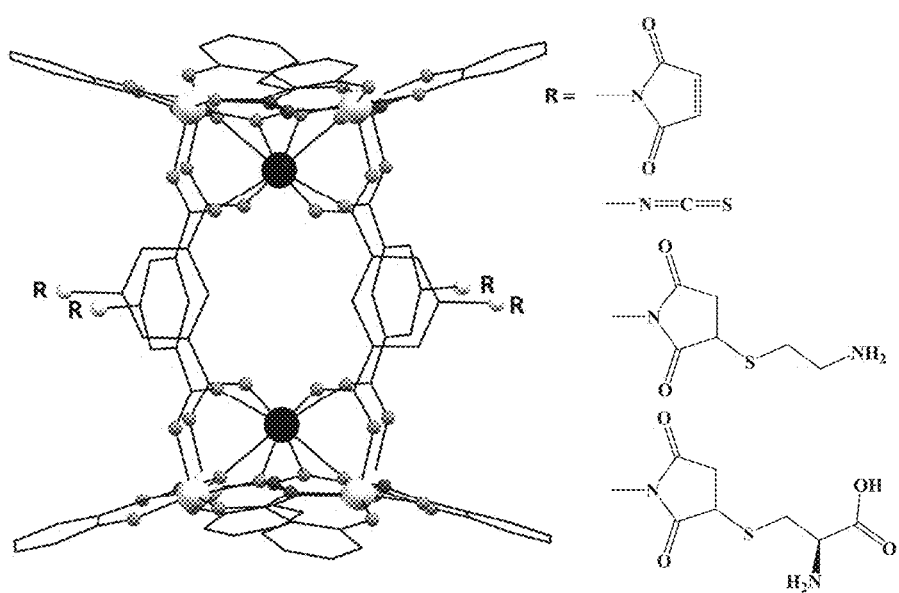
FIG. 26 is the crystal structure of possible modifications of Ga$_8$Ln$_2$(shi)$_8$ structure on bridging isophthalate ligands.

The UV-Vis spectroscopy data for the $H_3shi$ and the $Ga_6Ln(shi)_9$ MCs in methanol solution are shown in FIG. 20, and the luminescence data for $Ga_6Ln(shi)_9$ are shown in FIGS. 21A and 21B.

Table 6 depicts the photophysical parameters of some of the solid state $Ga_6Ln(shi)_9$ complexes.

TABLE 6

Photophysical data of $Ga_6Ln(shi)_9$ complexes in the solid state

| Compound | $Q_{Ln}{}^L$/% | $\tau/\mu s$ |
|---|---|---|
| $Ga_6Pr(shi)_9$ | $3.7(2) \cdot 10^{-3}$ | 0.063(1) |
| $Ga_6Nd(shi)_9$ | 0.171(5) | 0.71(1) |
| $Ga_6Sm(shi)_9$ | 1.64(9) | 70(1) |
| $Ga_6Tb(shi)_9$ | 0.189(3) | 20.7(5): 71% 4.54(6); 29% |
| $Ga_6Ho(shi)_9$ | $1.1(2) \cdot 10^{-3}$ | 0.037(1) |
| $Ga_6Er(shi)_9$ | $7.1(2) \cdot 10^{-3}$ | 0.905(8) |
| $Ga_6Yb(shi)_9$ | 0.65(3) | 7.26(2) |

Preparation of [$Ln_2Ga_8(shi)_8(mip)_4$]($CH_3OH)_8(C_5H_6N^+)_2$ Complexes

Preparation of 5-maleimidoisophthalic Acid ($H_2mip$)

5-aminoisophthalic acid hydrate (19.92 g, 0.10 mol) and maleic anhydride (9.81 g, 0.10 mol) were dissolved in 200 mL of DMF. The mixture was stirred for ~1 hour after which DMF was removed under vacuum. The obtained product was washed with acetone to give ~19.00 g of 5-[(3-carboxy-1-oxo-2-propen-1-yl)amino]isophthalic acid as a yellow powder. 2.79 g (0.01 mol) of 5-[(3-carboxy-1-oxo-2-propen-1-yl)amino]isophthalic acid was added in to the solution of acetic anhydride (15.0 mL) and sodium acetate trihydrate (0.68 g, 0.005 mol) and the mixture was stirred at 60° C. for 2.5 hours. Acetic anhydride was then removed under vacuum and water (20.00 mL) was added. The slurry mixture was stirred at 70° C. for another 2 hours, filtered, and washed with copious amount of water. The white solid obtained is dried under vacuum to give pure 5-maleimidoisophthalic acid. Yield: ~2.0 g. Elemental analysis (%) for $C_{12}H_7NO_6$ (Calcd): C, 55.10; (55.18); H, 2.71; (2.70); N, 5.48; (5.36). $^1$H-NMR (400 MHz, DMSO) δ (ppm) 8.49 (1H, s), 8.18 (2H, s), 7.24 (2H, s). $^{13}$C-NMR (400 MHz, DMSO) δ (ppm) 169.66, 166.18, 134.85, 132.60, 132.30, 130.81, 128.69.

Preparation of [Ln$_2$Ga$_8$(shi)$_8$(mip)$_4$](CH$_3$OH)$_8$(C$_5$H$_6$N$^+$)$_2$ 5-maleimidoisophthalic acid (0.26 g, 1.00 mmol) and [LnGa$_4$(shi)$_4$(C$_6$H$_5$CO$_2$)$_4$(C$_4$H$_4$N)(CH$_3$OH)] (0.20 mmol) were dissolved in DMF (20 mL). The mixture was stirred for 4 hours and DMF was evaporated under vacuum. The obtained powder was washed with copious amount of MeOH to give the pure product.

[Tb$_2$Ga$_8$(shi)$_8$(mip)$_4$](CH$_3$OH)$_8$(C$_5$H$_6$N$^+$)$_2$ (Tb$_2$Ga$_8$(mip)$_4$). Yield: 0.28 g (79%). ESI-MS, calc. for [M]$^{2-}$, C$_{104}$H$_{52}$Ga$_8$N$_{12}$O$_{48}$Tb$_2$, 1563.2; found, 1563.2. Anal. Calcd for C$_{122}$H$_{96}$Ga$_8$N$_{14}$O$_{56}$Yb$_2$: C, 41.51; H, 2.74; N, 5.56; found: C, 41.65; H, 2.61; N, 5.35.

Figure 27:
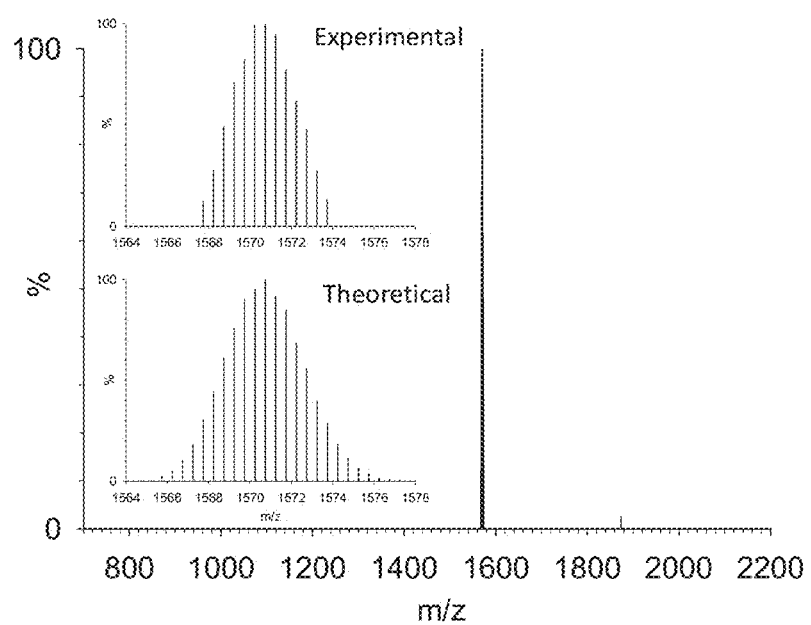
FIG. 27 concerns the mass-spectrum of [Yb$_2$Ga$_8$(shi)$_8$ (mip)$_4$](CH$_3$OH)$_8$(C$_5$H$_6$N$^+$)$_2$.

[Yb$_2$Ga$_8$(shi)$_8$(mip)$_4$](CH$_3$OH)$_8$(C$_5$H$_6$N$^+$)$_2$ (Yb$_2$Ga$_8$(mip)$_4$). Yield: 0.30 g (84%). ESI-MS, calc. for [M]$^{2-}$, C$_{104}$H$_{52}$Ga$_8$N$_{12}$O$_{48}$Yb$_2$, 1570.7; found, 1570.7; (FIG. 27). Anal. Calcd for C$_{122}$H$_{96}$Ga$_8$N$_{14}$O$_{56}$Yb$_2$: C, 41.18; H, 2.72; N, 5.51; found: C, 41.61; H, 2.60; N, 5.34.

Preparation of [Ln$_2$Ga$_8$(shi)$_8$(itip)$_4$](CH$_3$OH)$_8$(C$_5$H$_6$N$^+$)$_2$ Complexes Preparation of 5-isothiocyanateisophthalic Acid (H$_2$itip)

5-aminoisophthalic acid hydrate (1.17 g, 5.90 mmol) was dissolved in 12 mL acetone in which 25 mL solution of sodium acetate (1 M) in water was added. The mixture was cooled down to 0° C. and sodium hydroxide (0.50 g, 12.5 mmol) was added to yield a homogeneous solution. Thiophosgene (0.5 mL) was then added and the mixture was stirred for 30 minutes, after which the pH of the solution was adjusted to ~3 by hydrochloric acid. The precipitate was filtered and dissolved in acetone. The obtained solution was filtered and the filtrate was concentrated under vacuum to yield a white powder. Recrystallization in MeOH gave the pure product. Yield: 0.70 g. Elemental analysis (%) for C$_9$H$_5$NO$_4$S (Calcd): C, 48.51; (48.43); H, 2.32; (2.22); N, 6.40; (6.28).

$^1$H-NMR (400 MHz, DMSO) δ (ppm) 13.64 (2H, s), 8.37 (1H, s), 8.08 (2H, s). $^{13}$C-NMR (400 MHz, DMSO) δ (ppm) 165.61, 136.39, 133.27, 131.62, 130.44, 128.81.

Preparation of [Ln$_2$Ga$_8$(shi)$_8$(itip)$_4$](CH$_3$OH)$_8$(C$_5$H$_6$N$^+$)$_2$ 5-isothiocyanateisophthalic acid (0.036 g, 1.60 mmol) and

[LnGa$_4$(shi)$_4$(C$_6$H$_5$CO$_2$)$_4$(C$_5$H$_5$N)(CH$_3$OH)] (0.04 mmol) were dissolved in DMF (4 mL). The mixture was stirred for 4 hours and DMF was evaporated under vacuum. The obtained powder was washed with copious amount of MeOH to give the pure product.

[Tb$_2$Ga$_8$(shi)$_8$(itip)$_4$](CH$_3$OH)$_8$(C$_5$H$_6$N$^+$)$_2$ (Tb$_2$Ga$_8$(itip)$_4$). Yield: 0.019 g (28%). ESI- MS, calc. for [M]$^{2-}$, C$_{92}$H$_{44}$Ga8N$_{12}$O$_{40}$S$_4$Yb$_2$, 1479.7; found, 1479.7. Anal. Calcd for C$_{110}$H$_{88}$Ga$_8$N$_{14}$O$_{48}$S$_4$Tb$_2$: C, 39.11; H, 2.63; N, 5.81; found: C, 39.25; H, 2.61; N, 5.95.

Figure 28:
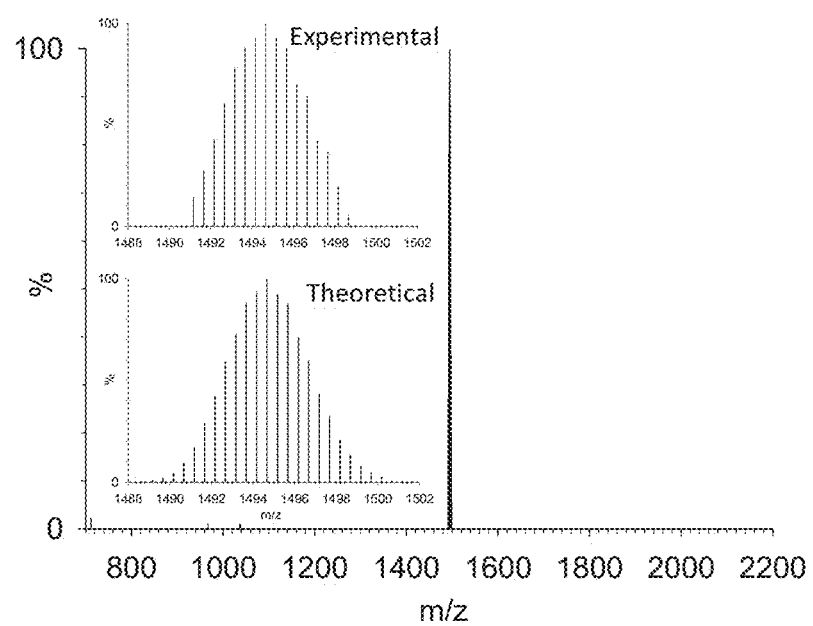
FIG. 28 concerns the mass-spectrum of [Yb$_2$Ga$_8$(shi)$_8$ (itip)$_4$](CH$_3$OH)$_8$(C$_5$H$_6$N$^+$)$_2$.

[Yb$_2$Ga$_8$(shi)$_8$(itip)$_4$](CH$_3$OH)$_8$(C$_5$H$_6$N$^+$)$_2$ (Yb$_2$Ga$_8$(itip)$_4$). Yield: 0.021 g (31%). ESI- MS, calc. for [M]$^{2-}$, C$_{92}$H$_{44}$Ga$_8$N$_{12}$O$_{40}$S$_4$Yb$_2$, 1494.7; found, 1494.7; (FIG. 28). Anal. Calcd for C$_{110}$H$_{88}$Ga$_8$N$_{14}$O$_{48}$S$_4$Yb$_2$: C, 38.79; H, 2.60; N, 5.76; found: C, 39.01; H, 2.66; N, 6.09.

Preparation of [Ln$_2$Ga$_8$(shi)$_8$(thiol-mip)$_4$](CH$_3$OH)$_8$(C$_5$H$_6$N$^+$)$_2$ Complexes

[Ln$_2$Ga$_8$(shi)$_8$(mip)$_4$](CH$_3$OH)$_8$(C$_5$H$_6$N$^+$)$_2$ (0.020 mmol) and a thiol-bearing compound (0.08 mmol) were mixed in 2 mL DMF. After 4 hours, DMF was evaporated under vacuum and the obtained powder was washed with MeOH to give the pure product.

Figure 29:
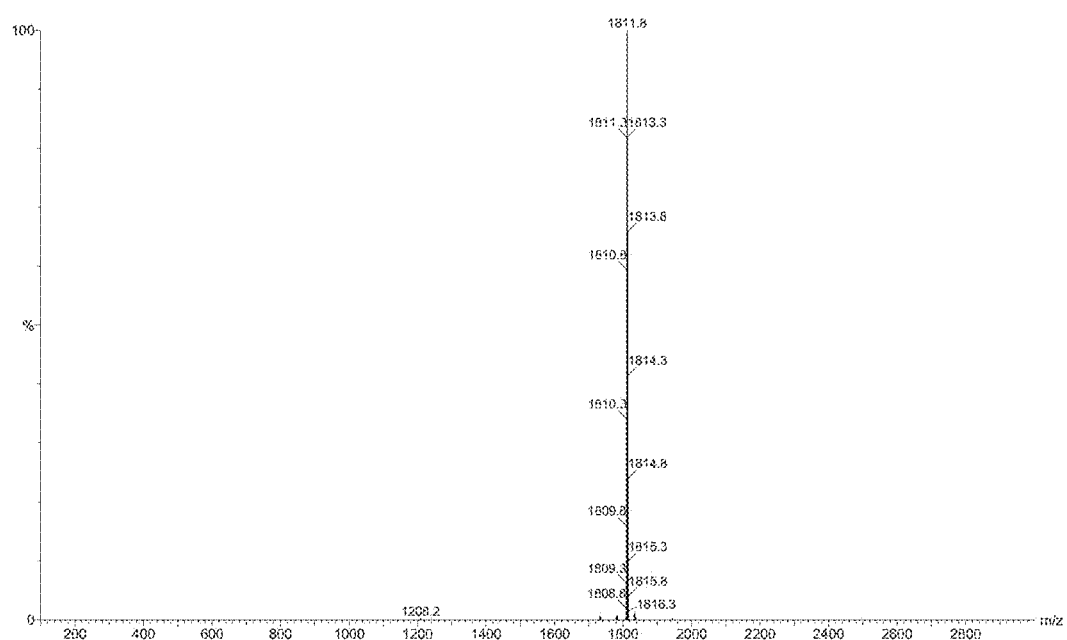
FIG. 29 concerns the mass-spectrum of [Yb$_2$Ga$_8$(shi)$_8$(L-cysteine-mip)$_4$](CH$_3$OH)$_8$(C$_5$H$_6$N$^+$)$_2$.

[Yb$_2$Ga$_8$(shi)$_8$(L-cysteine-mip)$_4$](CH$_3$OH)$_8$(C$_5$H$_6$N$^+$)$_2$ (Yb$_2$Ga$_8$(L-cysteine-mip)$_4$). Yield: 0.060 g (74%). ESI-MS, calc. for [M]$^{2-}$, C$_{116}$H$_{80}$Ga$_8$N$_{16}$O$_{56}$S$_4$Yb$_2$, 1812.7; found, 1811.8; (FIG. 29). Anal. Calcd for C$_{134}$H$_{124}$Ga$_8$N$_{18}$O$_{64}$S$_4$Yb$_2$: C, 39.81; H, 3.09; N, 6.24; found: C, 39.69; H, 3.10; N, 5.94.

Figure 30:
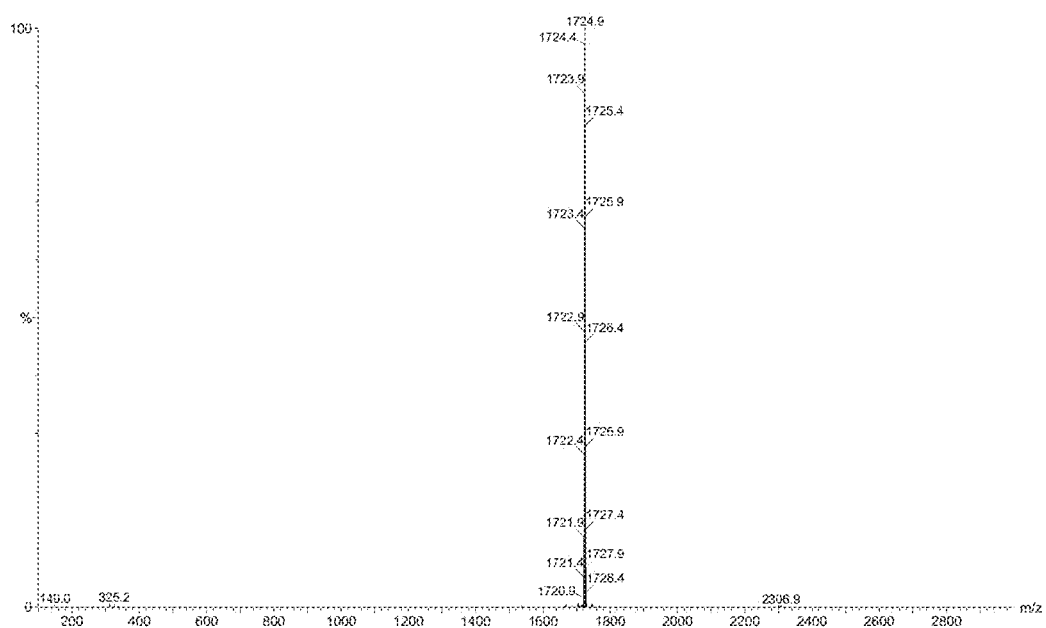
FIG. 30 concerns the mass-spectrum of Yb$_2$Ga$_8$(shi)$_8$ (cysteamine-mip)$_4$](CH$_3$OH)$_8$(C$_5$H$_6$N$^+$)$_2$.

[Yb$_2$Ga$_8$(shi)$_8$(cysteamine-mip)$_4$](CH$_3$OH)$_8$(C$_5$H$_6$N$^+$)$_2$ (Yb$_2$Ga$_8$(cysteamine-mip)$_4$). Yield: 0.065 g (83%). ESI-MS, calc. for [M]$^{2-}$, C$_{112}$H$_{80}$Ga$_8$N$_{16}$O$_{48}$S$_4$Yb$_2$, 1724.8; found, 1724.9; (FIG. 30). Anal. Calcd for C$_{130}$H$_{128}$Ga$_8$N$_{18}$O$_{58}$S$_4$Yb$_2$: C, 40.01; H, 3.31; N, 6.46; found: C, 40.36; H, 3.20; N, 6.74.

Preparation of [Na$_2$Ln$_2$Ga$_8$(shi)$_8$(sip)$_4$(H$_2$O)$_{10}$](C$_3$H$_7$NO)$_{14}$(NH$_4$)$_4$ Complexes H$_3$shi (306.3 mg, 2.0 mmol), Ln(NO$_3$)$_3$.xH$_2$O (0.50 mmol), Ga(NO$_3$)$_3$.xH$_2$O (511.5 mg, 2.0 mmol), and 5-sulfoisophthalic acid sodium salt (268.2 mg, 1.0 mmol) were dissolved in 18 mL DMF. Ammonium bicarbonate (632.5 mg, 8.0 mmol) was added to the solution and stirred overnight. The solution was filtered. Slow evaporation of the solution yielded crystalline compound after 1 month.

[Na$_2$Nd$_2$Ga$_8$(shi)$_8$(sip)$_4$(H$_2$O)$_{10}$](C$_3$H$_7$NO)$_{14}$(NH$_4$)$_4$ (Ga$_8$Nd$_2$(sip)$_4$). Yield: 351 mg (32%). Anal. Calcd for C$_{130}$H$_{178}$Ga$_8$N$_{26}$Na$_2$Nd$_2$O$_{76}$S$_4$: C, 35.97; H, 4.13; N, 8.39; found: C, 36.45; H, 4.45; N, 8.78.

[Na$_2$Sm$_2$Ga$_8$(shi)$_8$(sip)$_4$(H$_2$O)$_{10}$](C$_3$H$_7$NO)$_{14}$(NH$_4$)$_4$ (Ga$_8$Sm$_2$(sip)$_4$). Yield: 360 mg (33%). Anal. Calcd for C$_{130}$H$_{178}$Ga$_8$N$_{26}$Na$_2$Sm$_2$O$_{76}$S$_4$: C, 35.86; H, 4.12; N, 8.36; found: C, 36.37; H, 4.43; N, 8.78.

[Na$_2$Eu$_2$Ga$_8$(shi)$_8$(sip)$_4$(H$_2$O)$_{10}$](C$_3$H$_7$NO)$_{14}$(NH$_4$)$_4$ (Ga$_8$Eu$_2$(sip)$_4$). Yield: 320 mg (29%). Anal. Calcd for C$_{130}$H$_{178}$Ga$_8$N$_{26}$Na$_2$Eu$_2$O$_{76}$S$_4$: C, 35.84; H, 4.12; N, 8.36; found: C, 36.20; H, 4.38; N, 8.72.

[Na$_2$Gd$_2$Ga$_8$(shi)$_8$(sip)$_4$(H$_2$O)$_{10}$](C$_3$H$_7$NO)$_{14}$(NH$_4$)$_4$ (Ga$_8$Gd$_2$(sip)$_4$). Yield: 375 mg (34%). Anal. Calcd for C$_{130}$H$_{178}$Ga$_8$N$_{26}$Na$_2$Gd$_2$O$_{76}$S$_4$: C, 35.75; H, 4.11; N, 8.34; found: C, 36.18; H, 4.35; N, 8.74.

[Na$_2$Tb$_2$Ga$_8$(shi)$_8$(sip)$_4$(H$_2$O)$_{10}$](C$_3$H$_7$NO)$_{14}$(NH$_4$)$_4$ (Ga$_8$Tb$_2$(sip)$_4$). Yield: 367 mg (34%). Anal. Calcd for C$_{130}$H$_{178}$Ga$_8$N$_{26}$Na$_2$Tb$_2$O$_{76}$S$_4$: C, 35.72; H, 4.11; N, 8.33; found: C, 36.10; H, 4.35; N, 8.72.

[Na$_2$Dy$_2$Ga$_8$(shi)$_8$(sip)$_4$(H$_2$O)$_{10}$](C$_3$H$_7$NO)$_{14}$(NH$_4$)$_4$ (Ga$_8$Dy$_2$(sip)$_4$). Yield: 344 mg (31%). Anal. Calcd for C$_{130}$H$_{178}$Ga$_8$N$_{26}$Na$_2$Dy$_2$O$_{76}$S$_4$: C, 35.67; H, 4.10; N, 8.32; found: C, 36.07; H, 4.39; N, 8.72.

[Na$_2$Ho$_2$Ga$_8$(shi)$_8$(sip)$_4$(H$_2$O)$_{10}$](C$_3$H$_7$NO)$_{14}$(NH$_4$)$_4$ (Ga$_8$Ho$_2$(sip)$_4$). Yield: 343 mg (31%). Anal. Calcd for C$_{130}$H$_{178}$Ga$_8$N$_{26}$Na$_2$Ho$_2$O$_{76}$S$_4$: C, 35.63; H, 4.09; N, 8.31; found: C, 35.42; H, 4.32; N, 8.55.

[Na$_2$Er$_2$Ga$_8$(shi)$_8$(sip)$_4$(H$_2$O)$_{10}$](C$_3$H$_7$NO)$_{14}$(NH$_4$)$_4$ (Ga$_8$Er$_2$(sip)$_4$). Yield: 311 mg (28%). Anal. Calcd for C$_{130}$H$_{178}$Ga$_8$N$_{26}$Na$_2$Er$_2$O$_{76}$S$_4$: C, 35.59; H, 4.09; N, 8.30; found: C, 35.72; H, 4.31; N, 8.50.

[Na$_2$Tm$_2$Ga$_8$(shi)$_8$(sip)$_4$(H$_2$O)$_{10}$](C$_3$H$_7$NO)$_{14}$(NH$_4$)$_4$ (Ga$_8$Tm$_2$(sip)$_4$). Yield: 332 mg (30%). Anal. Calcd for C$_{130}$H$_{178}$Ga$_8$N$_{26}$Na$_2$Tm$_2$O$_{76}$S$_4$: C, 35.56; H, 4.09; N, 8.29; found: C, 35.56; H, 4.44; N, 8.51.

[Na$_2$Yb$_2$Ga$_8$(shi)$_8$(sip)$_4$(H$_2$O)$_{10}$](C$_3$H$_7$NO)$_{14}$(NH$_4$)$_4$ (Ga$_8$Yb$_2$(sip)$_4$). Yield: 337 mg (31%). Anal. Calcd for C$_{130}$H$_{178}$Ga$_8$N$_{26}$Na$_2$Yb$_2$O$_{76}$S$_4$: C, 35.49; H, 4.08; N, 8.28; found: C, 35.52; H, 4.40; N, 8.56.

As illustrated throughout the examples, upon excitation through their organic chromophoric moieties, the heterometallic metallacrowns disclosed herein exhibited remarkable luminescence properties across the visible and near-infrared (NIR) regions. In some instances, the remarkable luminescence properties were in spite of the presence of solvent molecules bound in the first sphere of coordination of Ln$^{3+}$ ions. It is believed that the sensitization efficiency in this system is sufficiently high, and thus outweighs the contribution of the quenching process. Several complexes of this series (e.g., Ga$_4$Yb(shi)$_4$, and Ga$_4$Er(shi)$_4$) display the highest reported quantum efficiencies values in the solid state (in comparison to other lanthanide complexes formed with organic ligands currently described in the literature). In solution, interactions with the solvent take an increased importance, lowering the luminescence intensity through non-radiative quenching processes. The examples disclosed herein also demonstrate NIR luminescence for a Dy$^{3+}$ (Ga$_4$Dy(shi)$_4$,) complex formed with the metallacrown in solution, as well as the less common visible and NIR luminescence, respectively, for Tm$^{3+}$ and Ho$^{3+}$ (Ga$_4$Tm(shi)$_4$, and Ga$_4$Ho(shi)$_4$,) in metallacrown complexes in the solid state.

The luminescent lanthanide complexes disclosed herein hold great promise for bioanalytical assays and biological imaging as their optical properties have several advantages over classical organic fluorophores and semi-conductor nanoparticles. Attractive luminescence characteristics include long luminescence lifetimes, large energy differences between excitation and emission bands and sharp emission bands throughout the visible and near-infrared (NIR) spectral ranges. These emission bands do not overlap and their wavelength positions are not affected by variation of the local microenvironment, such as changes in polarity, temperature, pH, or interactions with biological media. It is believed that the luminescent lanthanide complexes disclosed herein also do not photobleach.

The complexes disclosed herein, with such strong NIR luminescence, may be suitable for use in a broad range of applications including bioanalytical assays, biological imaging, telecommunications, energy conversion, barcodes, and optical materials. Additionally, these complexes have potential for multi-modal applications. Coupled with the strong luminescence, the presence of Ga$^{3+}$ ions allows for use of radioactive gallium for positron emission tomography (Ga-68) or single-photon emission computed tomography (Ga-67). The lanthanide ion in this system also has access to approximately one solvent molecule (q=1) which opens the opportunity for imaging via magnetic resonance techniques (MRI, CEST, etc).

It is to be understood that any ranges provided herein include the stated range and any value or sub-range within the stated range. Furthermore, when "about" is utilized to describe a value, this is meant to encompass minor variations (up to +/−10%) from the stated value.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

In describing and claiming the examples disclosed herein, the singular forms "a", "an", and "the" include plural referents unless the context clearly dictates otherwise.

While several examples have been described in detail, it will be apparent to those skilled in the art that the disclosed examples may be modified. Therefore, the foregoing description is to be considered non-limiting.

The invention claimed is:

1. A heterometallic metallacrown compound incorporating Ga(III) and Ln(III) cations, with a templating ligand being isophthalic acid, salicylic hydroxamic acid or derivatives thereof, wherein said metallacrown contains at least one repeating [—Ga—N—O—] sub-unit where the N—O derives from the templating ligand.

2. The heterometallic metallacrown compound of claim 1, including a Ln(III)[12-MC$_{Ga^{III}N(shi)}$-4] core, wherein MC$_{Ga^{III}N(shi)}$ is a metallacrown macrocycle with a repeating sub-unit consisting of Ga(III) ion and a salicylic hydroxamic acid (H$_3$shi) ligand or its derivatives.

3. The heterometallic metallacrown compound of any one of claims 1 to 2, including at least one countercation (C$^+$) which balances the charge of the compound.

4. The heterometallic metallacrown compound of claim 1, having the formula: Ln(III)(OX)$_4$[12-MC$_{Ga^{III}N(shi)}$-4](C$^+$), wherein MC$_{Ga^{III}N(shi)}$ is a metallacrown macrocycle with a repeating sub-unit consisting of Ga(III) ion and a salicylic hydroxamic acid (H$_3$shi) ligand or its derivatives, OX$^-$ are bridging carboxylate units and C+ are countercations that balance the charge of the compound.

5. The heterometallic metallacrown compound of claim 1, having the formula: Ln$_2$(isophthalate)$_4$[12-MC$_{GaNshi}$-4]$_2$.

6. The heterometallic metallacrown compound of claim 1, having the formula: Ln$^{3+}$ [12-MC$_{Ga^{III}N(shi)}$-4].

7. The heterometallic metallacrown compound of claim 1, having the formula: Ga$_6$Ln(shi)$_9$.

8. The heterometallic metallacrown compound of claim 1, wherein Ln(III) is chosen from the lanthanide ions consisting of: yttrium (Y$^{3+}$), lanthanum (La$^{3+}$), cerium (Ce$^{3+}$), praseodymium (Pr$^{3+}$), neodymium (Nd$^{3+}$), promethium (Pm$^{3+}$), samarium (Sm$^{3+}$), europium (Eu$^{3+}$), gadolinium (Gd$^{3+}$), terbium (Tb$^{3+}$), dysprosium (Dy$^{3+}$), holmium (Ho$^{3+}$), erbium (Er$^{3+}$), thulium (Tm$^{3+}$), ytterbium (Yb$^{3+}$), and lutetium (Lu$^{3+}$).

9. A method for bioanalytical assay or biological imaging, comprising contacting cells with the heterometallic metallacrown compound of claim 1.

10. The heterometallic metallacrown compound of claim 1, wherein the derivatives of salicylic hydroxamic acid have the following formula:

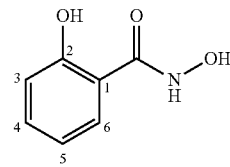

with any combination of R-groups bound at each of positions 3 through 6, each R-group being independently selected from the group consisting of —H, -D, —OH, —SH, —NH$_2$, —NO$_2$, —F, —Cl, —Br, —I, —CF$_3$, —OCH$_3$, —SO$_3$H, —CH$_3$, —CN, a fused aromatic ring, a fused heterocyclic ring, an amide, =O, =N, —N$_3$, —NR'H, —NR'2, —NR'$^{3+}$, —COOH, —COOR', —CH$_2$—R', —CHR$_2$, —CHR'R", —CR'R"R'", —OR', and combinations thereof, wherein R', R", and R'" are independently selected from the group consisting of —H, -D, a fused aromatic ring, and a fused heterocyclic ring.

11. The heterometallic metallacrown compound of claim 1, wherein the derivatives of isophthalic acid have the following formula:

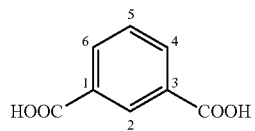

with any combination of R-groups bound at each of positions 2, and 4 through 6, each R-group being independently selected from the group consisting of —H, -D, —OH, —SH, —NH$_2$, —NO$_2$, —F, —Cl, —Br, —I, —CF$_3$, —OCH$_3$, —SO$_3$H, —CH$_3$, —CN, a fused aromatic ring, a fused heterocyclic ring, an amide, =O, =N, —N$_3$, —NR'H, —NR'2, —NR'$^{3+}$, —COOH, —COOR', —CH$_2$—R', —CHR$_2$, —CHR'R", —CR'R"R'", —OR', and combinations thereof, wherein R', R", and R'" are independently selected from the group consisting of —H, -D, a fused aromatic ring, and a fused heterocyclic ring.

\* \* \* \* \*

UNITED STATES PATENT AND TRADEMARK OFFICE
CERTIFICATE OF CORRECTION

PATENT NO. : 10,562,920 B2  
APPLICATION NO. : 15/566058  
DATED : February 18, 2020  
INVENTOR(S) : Evan R. Trivedi et al.

Page 1 of 1

It is certified that error appears in the above-identified patent and that said Letters Patent is hereby corrected as shown below:

In the Specification

Column 1, after "LN(III) AND GA(III) METALLACROWN COMPLEXES" and before Line 4 please insert the following heading and paragraph:
--STATEMENT REGARDING FEDERALLY SPONSORED RESEARCH OR DEVELOPMENT
This invention was made with government support under CHE1057331 awarded by the National Science Foundation and GM102980 awarded by the National Institutes of Health. The government has certain rights in the invention.--

Signed and Sealed this
Twenty-sixth Day of January, 2021

Drew Hirshfeld
*Performing the Functions and Duties of the*
*Under Secretary of Commerce for Intellectual Property and*
*Director of the United States Patent and Trademark Office*